United States Patent
Wang et al.

(10) Patent No.: US 12,005,207 B2
(45) Date of Patent: Jun. 11, 2024

(54) CHEMICAL ABLATION AND METHOD OF TREATMENT FOR VARIOUS DISEASES

(71) Applicant: Neurotronic, Inc., Plymouth, MN (US)

(72) Inventors: Lixiao Wang, Henderson, NV (US); John J. Chen, Plymouth, MN (US); Yongxing Zhang, Irvine, CA (US)

(73) Assignee: Neurotronic, Inc., Plymouth, MN (US)

( * ) Notice: Subject to any disclaimer, the term of this patent is extended or adjusted under 35 U.S.C. 154(b) by 801 days.

(21) Appl. No.: 16/986,717

(22) Filed: Aug. 6, 2020

(65) Prior Publication Data

US 2020/0360671 A1 Nov. 19, 2020

Related U.S. Application Data

(63) Continuation of application No. 16/563,213, filed on Sep. 6, 2019, now Pat. No. 11,648,378, which is a
(Continued)

(51) Int. Cl.
*A61M 25/10* (2013.01)
*A61B 18/06* (2006.01)
(Continued)

(52) U.S. Cl.
CPC ......... *A61M 25/1002* (2013.01); *A61B 18/06* (2013.01); *A61K 31/045* (2013.01);
(Continued)

(58) Field of Classification Search
None
See application file for complete search history.

(56) References Cited

U.S. PATENT DOCUMENTS

| 4,254,056 A * | 3/1981 | Konno ............... A61P 29/00 564/387 |
| 4,573,966 A | 3/1986 | Weikl et al. |

(Continued)

FOREIGN PATENT DOCUMENTS

| CN | 1593359 A | 3/2005 |
| CN | 101035593 A | 9/2007 |

(Continued)

OTHER PUBLICATIONS

"U.S. Appl. No. 16/563,192, Notice of Allowance dated Mar. 8, 2023", 8 pgs.
(Continued)

*Primary Examiner* — Manuel A Mendez
(74) *Attorney, Agent, or Firm* — Schwegman, Lundberg & Woessner, P.A.

(57) ABSTRACT

Embodiments of the present invention provide a device and a method for treating at least one of hypertension, pulmonary arteries, diabetes, obesity, heart failure, end-stage renal disease, digestive disease, urological disease, cancers, tumors, pain, asthma or chronic obstructive pulmonary disease by delivering an effective amount of a formulation to a tissue. In embodiments of the present invention, the formulation may include at least one of a gas, a vapor, a liquid, a solution, an emulsion, or a suspensions of one or more ingredients. In embodiments of the present invention, amounts of the formulation and/or energy are effective to injure or damage tissue, nerves, and nerve endings in order to relieve disease symptoms.

8 Claims, 18 Drawing Sheets

Related U.S. Application Data continuation of application No. 16/156,163, filed on Oct. 10, 2018, now Pat. No. 10,758,713, which is a continuation of application No. 15/521,973, filed as application No. PCT/US2015/058296 on Oct. 30, 2015, now Pat. No. 10,286,191.

(60) Provisional application No. 62/124,868, filed on Jan. 5, 2015, provisional application No. 62/122,818, filed on Oct. 30, 2014.

(51) Int. Cl.
| | | |
|---|---|---|
| *A61K 31/045* | (2006.01) | |
| *A61M 5/00* | (2006.01) | |
| *A61M 5/142* | (2006.01) | |
| *A61M 5/172* | (2006.01) | |
| *A61M 29/02* | (2006.01) | |
| *A61B 18/00* | (2006.01) | |

(52) U.S. Cl.
CPC ............ *A61M 5/007* (2013.01); *A61M 5/142* (2013.01); *A61M 5/172* (2013.01); *A61M 25/1011* (2013.01); *A61M 29/02* (2013.01); *A61B 2018/00577* (2013.01); *A61M 2025/105* (2013.01); *A61M 2025/1052* (2013.01); *A61M 2202/02* (2013.01)

(56) References Cited

U.S. PATENT DOCUMENTS

| | | | |
|---|---|---|---|
| 4,653,438 A | 3/1987 | Russell | |
| 5,045,061 A | 9/1991 | Seifert et al. | |
| 5,263,931 A | 11/1993 | Miller | |
| 5,314,443 A | 5/1994 | Rudnick | |
| 5,315,992 A | 5/1994 | Dalton | |
| 5,380,284 A | 1/1995 | Don | |
| 5,419,763 A | 5/1995 | Hildebrand | |
| 5,423,755 A | 6/1995 | Kesten et al. | |
| 5,460,610 A | 10/1995 | Don | |
| 5,599,307 A * | 2/1997 | Bacher | A61M 25/104 |
| | | | 604/509 |
| 5,681,281 A | 10/1997 | Vigil et al. | |
| 5,720,735 A | 2/1998 | Dorros | |
| 6,048,332 A | 4/2000 | Duffy et al. | |
| 6,062,223 A | 5/2000 | Palazzo et al. | |
| 6,135,981 A | 10/2000 | Dyke | |
| 6,148,222 A * | 11/2000 | Ramsey, III | A61N 1/0517 |
| | | | 607/116 |
| 6,258,087 B1 | 7/2001 | Edwards et al. | |
| 6,623,452 B2 | 9/2003 | Chien et al. | |
| 6,685,672 B1 | 2/2004 | Forman | |
| 7,617,005 B2 | 11/2009 | Demarais et al. | |
| 7,653,438 B2 | 1/2010 | Deem et al. | |
| 7,717,948 B2 | 5/2010 | Demarais et al. | |
| 8,052,668 B2 | 11/2011 | Sih | |
| 8,372,054 B2 | 2/2013 | Duffy et al. | |
| 8,740,849 B1 * | 6/2014 | Fischell | A61M 25/0084 |
| | | | 604/173 |
| 8,774,913 B2 | 7/2014 | Demarais et al. | |
| 8,840,601 B2 | 9/2014 | Salahieh et al. | |
| 9,114,123 B2 | 8/2015 | Vafai et al. | |
| 10,286,191 B2 | 5/2019 | Wang et al. | |
| 10,537,375 B2 | 1/2020 | Wang | |
| 10,758,713 B2 | 9/2020 | Wang et al. | |
| 11,382,689 B2 | 7/2022 | Wang | |
| 11,517,725 B2 | 12/2022 | Wang et al. | |
| 11,648,378 B2 | 5/2023 | Wang et al. | |
| 11,684,417 B2 | 6/2023 | Wang | |
| 2002/0014238 A1 | 2/2002 | Kotmel | |
| 2002/0068953 A1 | 6/2002 | Kokish | |
| 2002/0177846 A1 | 11/2002 | Mulier | |
| 2003/0066532 A1 | 4/2003 | Gobel | |
| 2004/0267336 A1 | 12/2004 | Morrison et al. | |
| 2005/0288639 A1 * | 12/2005 | Hibner | A61M 25/04 |
| | | | 600/29 |
| 2006/0161233 A1 | 7/2006 | Barry et al. | |
| 2006/0235474 A1 | 10/2006 | Demarais | |
| 2006/0265014 A1 | 11/2006 | Demarais et al. | |
| 2006/0282120 A1 | 12/2006 | Sih | |
| 2007/0077230 A1 | 4/2007 | Mon | |
| 2008/0114297 A1 | 5/2008 | Barry et al. | |
| 2008/0118544 A1 | 5/2008 | Wang | |
| 2008/0208118 A1 | 8/2008 | Goldman | |
| 2008/0255508 A1 | 10/2008 | Wang | |
| 2008/0255509 A1 | 10/2008 | Wang | |
| 2009/0192505 A1 | 7/2009 | Askew et al. | |
| 2009/0301483 A1 | 12/2009 | Barry et al. | |
| 2010/0010470 A1 | 1/2010 | Bates | |
| 2010/0087781 A1 * | 4/2010 | Adams | A61B 18/04 |
| | | | 604/101.03 |
| 2010/0145304 A1 | 6/2010 | Cressman | |
| 2010/0209472 A1 | 8/2010 | Wang | |
| 2011/0104061 A1 | 5/2011 | Seward | |
| 2011/0152683 A1 | 6/2011 | Gerrans et al. | |
| 2011/0182912 A1 | 7/2011 | Evans et al. | |
| 2011/0218564 A1 | 9/2011 | Drasler et al. | |
| 2012/0083809 A1 | 4/2012 | Drasler et al. | |
| 2012/0116438 A1 | 5/2012 | Salahieh et al. | |
| 2012/0197245 A1 | 8/2012 | Burnett et al. | |
| 2012/0209251 A1 | 8/2012 | Bates | |
| 2012/0215212 A1 | 8/2012 | Selzer et al. | |
| 2012/0259269 A1 | 10/2012 | Meyer | |
| 2012/0271277 A1 | 10/2012 | Fischell et al. | |
| 2012/0271301 A1 | 10/2012 | Fischell et al. | |
| 2013/0138082 A1 * | 5/2013 | Salahieh | A61M 25/10 |
| | | | 604/509 |
| 2013/0178910 A1 * | 7/2013 | Azamian | A61B 17/32 |
| | | | 607/33 |
| 2013/0189190 A1 | 7/2013 | Wang | |
| 2015/0056298 A1 | 2/2015 | Azamian et al. | |
| 2015/0272666 A1 | 10/2015 | Wang | |
| 2016/0135879 A1 * | 5/2016 | Beasley | A61M 25/0054 |
| | | | 606/41 |
| 2016/0310200 A1 | 10/2016 | Wang | |
| 2018/0015264 A1 | 1/2018 | Wang et al. | |
| 2019/0015639 A1 | 1/2019 | Wang et al. | |
| 2019/0038881 A1 | 2/2019 | Wang et al. | |
| 2019/0307507 A1 | 10/2019 | Wang | |
| 2019/0388147 A1 | 12/2019 | Wang | |
| 2020/0009355 A1 | 1/2020 | Wang et al. | |
| 2020/0016379 A1 | 1/2020 | Wang et al. | |
| 2020/0086093 A1 | 3/2020 | Wang | |
| 2020/0398032 A1 | 12/2020 | Wang et al. | |
| 2021/0275784 A1 | 9/2021 | Wang | |
| 2021/0275785 A1 | 9/2021 | Wang | |
| 2021/0275786 A1 | 9/2021 | Wang | |
| 2021/0275787 A1 | 9/2021 | Wang | |
| 2022/0233827 A1 | 7/2022 | Wang et al. | |
| 2023/0270489 A1 | 8/2023 | Wang | |

FOREIGN PATENT DOCUMENTS

| | | |
|---|---|---|
| CN | 101861184 A | 10/2010 |
| CN | 102481428 A | 5/2012 |
| CN | 102573466 A | 7/2012 |
| CN | 102600546 A | 7/2012 |
| CN | 102698354 A | 10/2012 |
| CN | 102727986 A | 10/2012 |
| CN | 102743163 A | 10/2012 |
| CN | 107106820 A | 8/2017 |
| CN | 110772311 A | 2/2020 |
| CN | 113040895 | 6/2021 |
| EP | 2497524 A1 | 9/2012 |
| EP | 2914326 B1 | 8/2023 |
| JP | S5769814 A | 4/1982 |
| JP | H04215767 A | 8/1992 |
| JP | H07308382 A | 11/1995 |
| JP | 08508917 A | 9/1996 |
| JP | 2000279524 | 10/2000 |
| JP | 2004035128 A | 2/2004 |
| JP | 2004180892 A | 7/2004 |

(56) References Cited

FOREIGN PATENT DOCUMENTS

| JP | 2004528924 A | 9/2004 |
|---|---|---|
| JP | 2005506101 A | 3/2005 |
| JP | 2006502801 A | 1/2006 |
| JP | 2010078379 A | 4/2010 |
| JP | 2010519005 A | 6/2010 |
| JP | 2010528815 A | 8/2010 |
| JP | 2011519699 A | 7/2011 |
| JP | 2012505050 A | 3/2012 |
| JP | 2012508067 A | 4/2012 |
| JP | 2012517858 A | 8/2012 |
| JP | 2012524808 A | 10/2012 |
| JP | 2013517847 A | 5/2013 |
| JP | 2014524342 A | 9/2014 |
| JP | 2014527272 A | 10/2014 |
| JP | 2015536945 | 12/2015 |
| JP | 2017533036 A | 11/2017 |
| JP | 6389185 B2 | 8/2018 |
| JP | 2018153239 A | 10/2018 |
| JP | 2020189858 | 11/2020 |
| JP | 2021046397 | 3/2021 |
| JP | 2023027052 A | 3/2023 |
| WO | WO-9421320 A1 | 9/1994 |
| WO | WO-9618427 A1 | 6/1996 |
| WO | WO-9717099 A1 | 5/1997 |
| WO | WO-0119445 A1 | 3/2001 |
| WO | WO-02051490 A1 | 7/2002 |
| WO | WO-2006055695 A1 | 5/2006 |
| WO | WO-2008106357 A1 | 9/2008 |
| WO | WO-2009076732 A1 | 6/2009 |
| WO | WO-2009082433 A2 | 7/2009 |
| WO | WO-2010033686 A1 | 3/2010 |
| WO | WO-2010124120 A1 | 10/2010 |
| WO | WO-2011094367 A1 | 8/2011 |
| WO | WO-2011119159 A1 | 9/2011 |
| WO | WO-2013026565 A1 | 2/2013 |
| WO | WO-2013028781 A1 | 2/2013 |
| WO | 2013067382 | 5/2013 |
| WO | WO-2013090848 A1 | 6/2013 |
| WO | WO-2014070820 A2 | 5/2014 |
| WO | 2015058296 | 4/2015 |
| WO | WO-2016070032 A1 | 5/2016 |
| WO | WO-2023091475 A1 | 5/2023 |

OTHER PUBLICATIONS

"U.S. Appl. No. 16/563,192, Response filed Feb. 9, 2023 to Non Final Office Action dated Nov. 30, 2022", 13 pgs.
"U.S. Appl. No. 16/563,213, Notice of Allowability dated Mar. 1, 2023", 4 pgs.
"U.S. Appl. No. 16/563,213, Notice of Allowance dated Feb. 3, 2023", 7 pgs.
"U.S. Appl. No. 16/690,992, Non Final Office Action dated Feb. 6, 2023", 12 pgs.
"U.S. Appl. No. 16/690,992, Response filed Apr. 18, 2023 to Non Final Office Action dated Feb. 6, 2023", 14 pgs.
"Chinese Application Serial No. 201910917938.2, Decision of Rejection dated Mar. 14, 2023", w/ English translation, 13 pgs.
"Chinese Application Serial No. 201910917938.2, Response filed Feb. 27, 2023 to Office Action dated Oct. 18, 2022", w/ English Claims, 8 pgs.
"European Application Serial No. 13851462.5, Response filed Aug. 10, 2022 to Summons to Attend Oral Proceedings dated Feb. 28, 2022", 52 pgs.
"International Application Serial No. PCT/US2022/050087, International Search Report dated Mar. 1, 2023", 3 pgs.
"International Application Serial No. PCT/US2022/050087, Written Opinion dated Mar. 1, 2023", 4 pgs.
"Japanese Application Serial No. 2020-178075, Preliminary Examination Report dated Jan. 24, 2023", w/ English Translation, 2 pgs.
"Japanese Application Serial No. 2020-178075, Response field Dec. 21, 2022 to Office Action dated Nov. 22, 2022", w/English Translation, 11 pgs.

"U.S. Appl. No. 16/419,587, Non Final Office Action dated Oct. 5, 2021", 15 pgs.
"Effectiveness and Safety of Bronchial Thermoplasty in the Treatment of Severe Asthma", A Multicenter, Randomized, Double-Blind, Sham-Controlled Clinical Trial Am J Respir Crit Care Med vol. 181., (2010), 9 pgs.
"U.S. Appl. No. 16/419,587, Response filed Nov. 4, 2021 to Non Final Office Action dated Oct. 5, 2021", 12 pgs.
"U.S. Appl. No. 16/563,235, Response filed Nov. 16, 2021 to Non Final Office Action dated Sep. 30, 2021", 13 pgs.
"Japanese Application Serial No. 2018-153239, Response filed Nov. 16, 2021 to Notification of Reasons for Refusal dated Aug. 17, 2021", w Engilsh Claims, 10 pgs.
"Japanese Application Serial No. 2018-153239, Notification of Reasons for Refusal dated Jan. 5, 2022", w English Translation, 17 pgs.
"Japanese Application Serial No. 2020-178075, Notification of Reasons for Refusal dated Jan. 5, 2022", w English Translation, 8 pgs.
Dunican, Eleanor M, "Mucus plugs in patients with asthma linked to eosinophilia and airflow obstruction", J Clin Invest. 2018;128(3), (2018), 14 pgs.
Greer, M, "Paclitaxel-Coated Balloons in Refractory Nonanastomostic Airway Stenosis Following Lung Transplantation", American Journal of Transplantation 2014 14: 2400-2405, (2014), 2400-2405.
Kim, K. C., "Airway goblet cell mucin: its structure and regulation of secretion", Series Airway Mucus Eur Respir J 1997; 10:, (1997), pp. 2644-2649.
Krmisky, William, "Thermal ablation for asthma: current status and technique", J Thorac Dis 2017;9(Suppl 2):S104-S109, (2017), 6 pgs.
Menzella, Francesco, "Anti-IL5 Therapies for Severe Eosinophilic Asthma: Literature Review and Practical Insights", Journal of Asthma and Allergy 2020:13, (2020), 13 pgs.
Peters, Michael C, "Evidence for Exacerbation-Prone Asthma and Predictive Biomarkers of Exacerbation Frequency", Am J Respir Crit Care Med vol. 202, Iss 7, (2020), 10 pgs.
Sakata, Kenneth K, "Paclitaxel-coated balloon dilation for central airway obstruction", Respiratory Medicine Case Reports 24, (2018), 129-132.
"Japanese Application Serial No. 2017-523517, Office Action dated Jun. 23, 2020", w English translation, 14 pgs.
U.S. Appl. No. 14/438,411, filed Apr. 24, 2015, Chemical Ablation Formulations and Methods of Treatments for Various Diseases.
U.S. Appl. No. 16/419,587, filed May 22, 2019, Chemical Ablation Formulations and Methods of Treatments for Various Diseases.
U.S. Appl. No. 15/521,973, filed Apr. 26, 2017, U.S. Pat. No. 10,286,191, Chemical Ablation and Method of Treatment for Various Diseases.
U.S. Appl. No. 16/563,192, filed Sep. 6, 2019, Chemical Ablation Formulations and Methods of Treatments for Various Diseases.
U.S. Appl. No. 16/156,163, filed Oct. 10, 2018, Chemical Ablation and Method of Treatment for Various Diseases.
U.S. Appl. No. 16/563,213, filed Sep. 6, 2019, Chemical Ablation and Method of Treatment for Various Diseases.
U.S. Appl. No. 15/133,976, filed Apr. 20, 2016, U.S. Pat. No. 10,537,375, Chemical Ablation and Method of Treatment for Various Diseases.
U.S. Appl. No. 16/563,235, filed Sep. 6, 2019, Chemical Ablation and Method of Treatment for Various Diseases.
U.S. Appl. No. 16/690,992, filed Nov. 21, 2019, Chemical Ablation and Method of Treatment for Various Diseases.
"U.S. Appl. No. 16/690,992, Response filed Jul. 5, 2022 to Non Final Office Action dated Apr. 5, 2022", 19 pgs.
"Japanese Application Serial No. 202080044525.9, Examiners Decision of Final Refusal dated Jul. 5, 2022", w English Translation, 8 pgs.
"U.S. Appl. No. 16/690,992, Final Office Action dated Jul. 26, 2022", 12 pgs.
"U.S. Appl. No. 16/563,235, Response filed Aug. 11, 2022 to Non Final Office Action dated May 12, 2022", 11 pgs.
"U.S. Appl. No. 16/563,235, Notice of Allowance dated Aug. 26, 2022", 7 pgs.

(56) References Cited

OTHER PUBLICATIONS

"European Application Serial No. 15853911.4, Response filed Sep. 2, 2022 to Communication Pursuant to Article 94(3) EPC dated Apr. 28, 2022", 116 pgs.
"U.S. Appl. No. 16/563,213, Non Final Office Action dated Sep. 15, 2022", 9 pgs.
"European Application Serial No. 13851462.5, Summons to Attend Oral Proceedings dated Jan. 28, 2022", 10 pgs.
"European Application Serial No. 13851462.5, Summons to Attend Oral Proceedings dated Feb. 28, 2022", 4 pgs.
"Chinese Application Serial No. 201910917938.2, Office Action dated May 20, 2022", w English translation, 16 pgs.
"European Application Serial No. 15853911.4, Communication Pursuant to Article 94(3) EPC dated Apr. 28, 2022", 10 pgs.
"Japanese Application Serial No. 2020-134047, Examiners Decision of Final Refusal dated Jun. 21, 2022", w English translation, 6 pgs.
"U.S. Appl. No. 14/438,411, Advisory Action dated Apr. 30, 2019", 3 pgs.
"U.S. Appl. No. 14/438,411, Final Office Action dated Feb. 25, 2019", 15 pgs.
"U.S. Appl. No. 14/438,411, Final Office Action dated May 9, 2018", 9 pgs.
"U.S. Appl. No. 14/438,411, Non Final Office Action dated Sep. 21, 2018", 11 pgs.
"U.S. Appl. No. 14/438,411, Non Final Office Action dated Oct. 20, 2017", 9 pgs.
"U.S. Appl. No. 14/438,411, Preliminary Amendment filed Jul. 28, 2015", 9 pgs.
"U.S. Appl. No. 14/438,411, Response filed Jan. 17, 2018 to Non Final Office Action dated Oct. 20, 2017", 9 pgs.
"U.S. Appl. No. 14/438,411, Response filed Apr. 16, 2019 to Final Office Action dated Feb. 25, 2019", 18 pgs.
"U.S. Appl. No. 14/438,411, Response filed Aug. 7, 2018 to Final Office Action dated May 9, 2018", 12 pgs.
"U.S. Appl. No. 14/438,411, Response filed Aug. 25, 2017 to Restriction Requirement dated Jul. 14, 2017", 7 pgs.
"U.S. Appl. No. 14/438,411, Response filed Oct. 8, 2018 to Non Final Office Action dated Sep. 21, 2018", 17 pgs.
"U.S. Appl. No. 14/438,411, Restriction Requirement dated Jul. 14, 2017", 8 pgs.
"U.S. Appl. No. 15/133,976, Advisory Action dated Jul. 30, 2019", 7 pgs.
"U.S. Appl. No. 15/133,976, Corrected Notice of Allowability dated Nov. 20, 2019", 3 pgs.
"U.S. Appl. No. 15/133,976, Final Office Action dated May 3, 2019", 15 pgs.
"U.S. Appl. No. 15/133,976, Final Office Action dated Aug. 16, 2018", 26 pgs.
"U.S. Appl. No. 15/133,976, Non Final Office Action dated Feb. 15, 2018", 16 pgs.
"U.S. Appl. No. 15/133,976, Non Final Office Action dated Nov. 30, 2018", 14 pgs.
"U.S. Appl. No. 15/133,976, Notice of Allowance dated Oct. 1, 2019", 12 pgs.
"U.S. Appl. No. 15/133,976, Preliminary Amendment filed Apr. 20, 2016", 7 pgs.
"U.S. Appl. No. 15/133,976, Response filed Mar. 20, 2019 to Non Final Office Action dated Nov. 30, 2018", 17 pgs.
"U.S. Appl. No. 15/133,976, Response filed Jun. 14, 2018 to Non Final Office Action dated Feb. 15, 2018", 13 pgs.
"U.S. Appl. No. 15/133,976, Response filed Jul. 1, 2019 to Final Office Action dated May 3, 2019", 20 pgs.
"U.S. Appl. No. 15/133,976, Response filed Oct. 26, 2018 to Final Office Action dated Aug. 16, 2018", 20 pgs.
"U.S. Appl. No. 15/133,976, Response filed Dec. 27, 2017 to Restriction Requirement dated Oct. 31, 2017", 8 pgs.
"U.S. Appl. No. 15/133,976, Restriction Requirement dated Oct. 31, 2017", 7 pgs.
"U.S. Appl. No. 15/521,973, Examiner Interview Summary dated Jun. 4, 2018", 3 pgs.
"U.S. Appl. No. 15/521,973, Final Office Action dated Jan. 15, 2019", 16 pgs.
"U.S. Appl. No. 15/521,973, Non Final Office Action dated May 18, 2018", 21 pgs.
"U.S. Appl. No. 15/521,973, Non Final Office Action dated Sep. 14, 2018", 15 pgs.
"U.S. Appl. No. 15/521,973, Notice of Allowance dated Mar. 27, 2019", 7 pgs.
"U.S. Appl. No. 15/521,973, Preliminary Amendment filed Apr. 26, 2017", 8 pgs.
"U.S. Appl. No. 15/521,973, Response filed Mar. 14, 2019 to Final Office Action dated Jan. 15, 2019", 16 pgs.
"U.S. Appl. No. 15/521,973, Response filed Dec. 10, 2018 to Non Final Office Action dated Sep. 14, 2018", 11 pgs.
"U.S. Appl. No. 16/156,163, Non Final Office Action dated Apr. 2, 2020", 7 pgs.
"U.S. Appl. No. 16/156,163, Notice of Allowance dated Jul. 22, 2020", 5 pgs.
"U.S. Appl. No. 16/156,163, Response filed Jul. 1, 2020 to Non Final Office Action dated Apr. 2, 2020", 9 pgs.
"U.S. Appl. No. 16/419,587, Preliminary Amendment filed Jul. 9, 2019", 3 pgs.
"Chinese Application Serial No. 201380055918.X, Office Action dated Jan. 17, 2018", (English Translation), 8 pgs.
"Chinese Application Serial No. 201380055918.X, Office Action dated Feb. 19, 2019", W/ English Translation, 6 pgs.
"Chinese Application Serial No. 201380055918.X, Office Action dated May 19, 2017", w/ English Translation, 18 pgs.
"Chinese Application Serial No. 201380055918.X, Office Action dated Dec. 27, 2019", w/ English translation, 12 pgs.
"Chinese Application Serial No. 201380055918.X, Response filed Apr. 2, 2018 to Office Action dated Jan. 17, 2018", w/ English claims, 15 pgs.
"Chinese Application Serial No. 201380055918.X, Response filed Aug. 23, 2019 to Office Action dated Feb. 19, 2019", w/English Claims, 14 pgs.
"Chinese Application Serial No. 201380055918.X, Response filed Oct. 9, 2017 to Office Action dated May 19, 2017", w/ English Claims, 16 pgs.
"Chinese Application Serial No. 201380055918.X, Response filed 11-27-8 to Office Action mailed", w/English Claims, 16 pgs.
"Chinese Application Serial No. 201580058938.1, Office Action dated Jul. 2, 2020", w/ English translation, 14 pgs.
"Chinese Application Serial No. 201580058938.1, Office Action dated Sep. 3, 2019", W/English Translation, 17 pgs.
"Chinese Application Serial No. 201580058938.1, Response filed Mar. 18, 2020 to Office Action dated Sep. 3, 2019", w/English Claims, 15 pgs.
"Chinese Application Serial No. 201580058938.1, Voluntary Amendment dated Feb. 22, 2018", w/ English Claims, 21 pgs.
"European Application Serial No. 13851462.5, Communication Pursuant to Article 94(3) EPC dated Mar. 20, 2020", 7 pgs.
"European Application Serial No. 13851462.5, Communication Pursuant to Article 94(3) EPC dated Jun. 1, 2018", 9 pgs.
"European Application Serial No. 13851462.5, Extended European Search Report dated Jun. 6, 2016", 6 pgs.
"European Application Serial No. 13851462.5, Office Action dated Jun. 12, 2015", 3 pgs.
"European Application Serial No. 13851462.5, Response filed Jul. 20, 2020 to Communication Pursuant to Article 94(3) EPC dated Mar. 20, 2020", 13 pgs.
"European Application Serial No. 13851462.5, Response filed Oct. 19, 2015 to Office Action dated Jun. 12, 2015", 13 pgs.
"European Application Serial No. 13851462.5, Response filed Dec. 1, 2016 to Extended European Search Report dated Jun. 6, 2016", 20 pgs.
"European Application Serial No. 15853911.4, Communication Pursuant to Article 94(3) EPC dated Apr. 30, 2020", 8 pgs.
"European Application Serial No. 15853911.4, Extended European Search Report dated May 30, 2018", 15 pgs.

(56) References Cited

OTHER PUBLICATIONS

"European Application Serial No. 15853911.4, Reponse filed Nov. 12, 2018 to Extended European Search Report dated May 30, 2018", 17 pgs.
"International Application Serial No. PCT/US2015/058296, International Preliminary Report on Patentability dated May 11, 2017", 9 pgs.
"International Application Serial No. PCT/US2015/058296, International Search Report dated Jan. 21, 2016", 2 pgs.
"International Application Serial No. PCT/US2015/058296, Written Opinion dated Jan. 21, 2016", 7 pgs.
"Japanese Application Serial No. 2015-540733, Office Action dated Jul. 4, 2017", w/English Translation, 12 pgs.
"Japanese Application Serial No. 2015-540733, Office Action dated Dec. 29, 2017", With English Translation, 9 pgs.
"Japanese Application Serial No. 2015-540733, Response filed Mar. 16, 2018 to Office Action dated Dec. 29, 2017", w/ English Claims, 11 pgs.
"Japanese Application Serial No. 2015-540733, Response filed Oct. 4, 2017 to Office Action dated Jul. 4, 2017", w/ English Claims, 19 pgs.
"Japanese Application Serial No. 2017-523517, Notification of Reasons for Rejection dated Sep. 10, 2019", w/ English Translation, 13 pgs.
"Japanese Application Serial No. 2017-523517, Response filed Mar. 6, 2020 to Notification of Reasons for Rejection dated Sep. 10, 2019", w/English Claims, 14 pgs.
"Japanese Application Serial No. 2018-153239, Examiners Decision of Final Refusal dated Apr. 7, 2020", w/ English Translation, 9 pgs.
"Japanese Application Serial No. 2018-153239, Notification of Reasons for Refusal dated Jul. 2, 2019", W/ English Translation, 16 pgs.
"Japanese Application Serial No. 2018-153239, Response filed Oct. 1, 2019 to Notification of Reasons for Refusal dated Jul. 2, 2019", w/English Claims, 10 pgs.
Krum, H., et al., "Catheter-based renal sympathetic denervation for resistant hypertension: a multicentre safety and proof-of-principle cohort study.", Lancet, 373(9671), (2009), 2375-1281.
"U.S. Appl. No. 16/563,235, Notice of Allowance dated Feb. 11, 2022", 7 pgs.
"U.S. Appl. No. 16/419,587, Final Office Action dated Feb. 24, 2022", 18 pgs.
"U.S. Appl. No. 16/419,587, Response filed Mar. 9, 2022 to Final Office Action dated Feb. 24, 2022", 12 pgs.
"U.S. Appl. No. 16/690,992, Non Final Office Action dated Apr. 5, 2022", 23 pgs.
"U.S. Appl. No. 16/419,587, Notice of Allowance dated Apr. 11, 2022", 8 pgs.
"U.S. Appl. No. 16/419,587, Corrected Notice of Allowability dated Apr. 27, 2022", 5 pgs.
"Japanese Application Serial No. 2020-134047, Response filed Mar. 28, 2022 to Notification of Reasons for Refusal dated Sep. 28, 2021", w out English claims, Claims not amended in filed response, 21 pgs.
"Japanese Application Serial No. 2020-178075, Response filed Apr. 5, 2022 to Notification of Reasons for Refusal dated Jan. 5, 2022", w out English claims, Claims not amended in response filed, 5 pgs.
"Japanese Application Serial No. 2018-153239, Response filed Apr. 5, 2022 to Notification of Reasons for Refusal dated Jan. 5, 2022", w o English Claims, 8 pgs.
"U.S. Appl. No. 16/563,235, Non Final Office Action dated May 12, 2022", 16 pgs.
"Chinese Application Serial No. 201910917938.2, Response filed Sep. 28, 2022 to Office Action dated May 20, 2022", w English Claims, 7 pgs.
"U.S. Appl. No. 16/690,992, Response filed Oct. 26, 2022 to Final Office Action dated Jul. 26, 2022", 12 pgs.

"European Application Serial No. 13851462.5, Invitation pursuant to Article 94(3) and Rule 71(1) EPC dated Oct. 11, 2022", 4 pgs.
"Chinese Application Serial No. 201910917938.2, Office Action dated Oct. 18, 2022", w English translation, 7 pgs.
"Japanese Application Serial No. 2018-153239, Office Action dated Nov. 8, 2022", w English Translation, 45 pgs.
"Japanese Application Serial No. 202080044525.9, Response filed Nov. 7, 2022 to Examiners Decision of Final Refusal dated Jul. 5, 2022", w English Claims, 13 pgs.
"U.S. Appl. No. 16/563,192, Non Final Office Action dated Nov. 30, 2022", 21 pgs.
"U.S. Appl. No. 16/563,213, Response filed Dec. 13, 2022 to Non Final Office Action dated Sep. 15, 2022", 7 pgs.
"Japanese Application Serial No. 2017-523517, Response filed Oct. 23, 2020 to Office Action dated Jun. 23, 2020", w English Claims, 14 pgs.
"European Application Serial No. 15853911.4, Response filed Oct. 27, 2020 to Communication Pursuant to Article 94(3) EPC dated Apr. 30, 2020", 14 pgs.
"Chinese Application Serial No. 201580058938.1, Response filed Nov. 24, 2020 to Office Action dated Jul. 2, 2020", w English Claims, 16 pgs.
"Japanese Application Serial No. 2017-523517, Notification of Reasons for Refusal dated Jul. 6, 2021", w English Translation, 9 pgs.
"Japanese Application Serial No. 2018-153239, Notification of Reasons for Refusal dated Aug. 17, 2021", w English Translation, 17 pgs.
"Japanese Application Serial No. 2020-134047, Notification of Reasons for Refusal dated Sep. 28, 2021", w English Translation, 16 pgs.
"U.S. Appl. No. 16/563,235, Non Final Office Action dated Sep. 30, 2021", 13 pgs.
"U.S. Appl. No. 16/690,992, Advisory Action dated Jul. 26, 2023", 3 pgs.
"U.S. Appl. No. 16/690,992, Final Office Action dated May 15, 2023", 26 pgs.
"U.S. Appl. No. 16/690,992, Response filed Jul. 13, 2023 to Final Office Action dated May 15, 2023", 19 pgs.
"Chinese Application Serial No. 201910917938.2, Response filed Jun. 28, 23 to Decision of Rejection dated Mar. 14, 2023", w/ English Claims, 13 pgs.
"European Application Serial No. 23183741.0, Extended European Search Report dated Jul. 21, 2023", 14 pgs.
"Japanese Application Serial No. 2022-169101, Voluntary Amendment filed Jun. 19, 2023", 15 pgs.
Tian, Juanhua, et al., "Rectifying disorder of extracellularmatrix to suppress urethral stricture by protein nanofilm-controlled drug delivery from urinary catheter", nature communications, (May 17, 2023), 17 pgs.
"U.S. Appl. No. 16/690,992, Non Final Office Action dated Aug. 24, 2023", 23 pgs.
"U.S. Appl. No. 17/329,765, Restriction Requirement dated Sep. 13, 2023", 6 pgs.
"U.S. Appl. No. 17/329,795, Restriction Requirement dated Sep. 13, 2023", 6 pgs.
"U.S. Appl. No. 17/329,823, Restriction Requirement dated Sep. 13, 2023", 6 pgs.
"U.S. Appl. No. 17/329,842, Restriction Requirement dated Oct. 17, 2023", 6 pgs.
"Chinese Application Serial No. 202110227749.X, Office Action dated Dec. 22, 2023", w/ English Translation, 8 pgs.
"Japanese Application Serial No. 2022-169101, Notification of Reasons for Rejection dated Oct. 31, 2023", W/ English Translation, 9 pgs.
"Japanese Application Serial No. 2022-178135, Notification of Reasons for Refusal dated Nov. 11, 2023", w/ English Translation, 10 pgs.

* cited by examiner

CHEMICAL ABLATION AND METHOD OF TREATMENT FOR VARIOUS DISEASES

This application is a continuation of U.S. patent application Ser. No. 16/563,213, filed Sep. 6, 2019, which is a continuation of U.S. patent application Ser. No. 16/156,163, filed Oct. 10, 2018, which is a continuation of U.S. patent application Ser. No. 15/521,973, filed Apr. 26, 2017, which is a U.S. National Stage Filing under 35 U.S.C. 371 from International Application No. PCT/US2015/058296, filed Oct. 30, 2015, which claims priority to U.S. Provisional Patent Application No. 62/122,818, filed Oct. 30, 2014, and U.S. Provisional Patent Application No. 62/124,868, filed Jan. 5, 2015, the disclosures of each of which are hereby incorporated by reference in their entirety.

Embodiments of the present invention relate to chemical infusion devices, formulations and methods of treatment for hypertension, pulmonary hypertension, diabetes, obesity, heart failure, end-stage renal disease, digestive diseases, cancers, tumors, pain, asthma and chronic obstructive pulmonary disease (COPD). The devices can include a combination of a balloon and infusion catheter, as well as other delivery devices. The formulations can include gases, vapors, liquids, solutions, emulsions, and suspensions of one or more ingredients. The methods involve delivery of the formulations to targeted tissues in the human body by chemical infusion.

Hypertension, or high blood pressure, is a major global health concern. An estimated 30 to 40% of the adult population in the world suffers from this condition. Furthermore, its prevalence is expected to increase, especially in developing countries. Diagnosis and treatment of hypertension remain suboptimal, and most patients struggle to properly control blood pressure.

Benign prostatic hyperplasia is a non-cancerous enlargement of the prostate gland, which affects more than 50% percent of men over the age of 60. Early in life, the prostate is approximately the size of a walnut, weighing about 20 grams. Prostate enlargement, over time, is thought to be normal. With age, the prostate gradually increases to at least twice its original size. Prostate growth causes pressure to build against the neighboring urethra, leading to narrowing of this latter organ, and ultimately resulting in urinary obstruction which makes urinating difficult.

Chronic obstructive pulmonary disease (COPD) is associated with two major airflow obstruction disorders: chronic bronchitis and emphysema. Chronic bronchitis results from inflammation of the bronchial airways. The bronchial airways connect the trachea to the lungs. Emphysema is a disease, which results from over-inflation of alveoli, or the air sacs in the lungs. This condition causes shortness of breath. Approximately 16 million Americans suffer from COPD, the majority of which (80-90%) are lifetime smokers. COPD is a leading cause of death in the United States.

Asthma is a chronic respiratory disease characterized by excessive narrowing of the airways and caused by inflammation of the airways, excess mucus production and airway hyper responsiveness. This narrowing of the airways makes breathing difficult and can significantly impact patients' lives, limiting participation in numerous activities. In severe cases, asthma attacks can be life-threatening. To date, there is no known cure for asthma.

Chronic sinusitis (CS) results from inflammation of the membrane lining in one or more paranasal sinuses and is typically associated with significant tissue damage. Approximately 37 million cases of CS are reported annually to the Centers for Disease Control and Prevention (CDC).

Diabetes is a metabolic condition, or combination of conditions, where an individual experiences high concentrations of blood glucose. The condition is caused either by insufficient production of insulin within the body or by failure of cells to respond properly to insulin. Glycated hemoglobin (HbA1c) serves a marker of plasma glucose concentration and is clinically used for the diagnosis of diabetes. In humans, normal HbA1c levels are typically <6.0%, prediabetes HbA1c levels range from 6.0 to 6.4%, and diabetes HbA1c levels exceed 6.5%.

Diabetes is one of the leading causes of death and disability in the United States and in other developed countries. It is associated with long-term complications that affect almost every part of the body. It has been linked, for instance, to blindness, heart and blood vessel disease, stroke, kidney failure, amputations, and nerve damage.

Within the United States, diabetes affects approximately 8 percent of the population and has resulted in costs that approach $250 billion.

Diabetes is typically classified as either type 1 (also referred to as insulin-dependent diabetes or juvenile diabetes), wherein the patient fails to produce sufficient insulin, type 2 (also referred to as non-insulin-dependent diabetes, adult-onset diabetes, or obesity-related diabetes), wherein the patient fails to respond properly to insulin, or gestational diabetes, a condition which develops late in pregnant women.

Type 2 diabetes is the most common form of diabetes, accounting for 90 to 95% of overall cases. It is generally associated with older age, obesity, family history, previous history with gestational diabetes, and physical inactivity. It is also more prevalent in certain ethnicities. Type 2 diabetes is also referred to as insulin-resistant diabetes, as the pancreas typically produces sufficient amounts of insulin, but the body fails to respond properly it. Symptoms associated with type 2 diabetes include fatigue, frequent urination, increased thirst and hunger, weight loss, blurred vision, and slow healing of wounds or sores.

Obesity is another significant health concern, particularly in the developed world. It is a complex, multifactorial and chronic condition characterized by excess body fat, which results from an imbalance between energy expenditure and caloric intake. Although the causes of this imbalance are not completely understood, genetic and/or acquired physiologic events and environmental factors are thought to contribute. The adverse health effects associated with obesity, and more specifically morbid obesity, have become well-established in recent years. Such adverse effects include, but are not limited to, cardiovascular disease, diabetes, high blood pressure, arthritis, and sleep apnea. Generally, as a patient's body mass index (BMI) rises, the likelihood of suffering the adverse effects linked to obesity also rises.

The present invention provides new devices and methods for the treatment of hypertension, diabetes, obesity, heart failure, end-stage renal disease, digestive disease, urological disease, cancers, tumors, pain, asthma and chronic obstructive pulmonary disease (COPD). The new methods involve chemical infusion formulations and delivery systems and strategies. The methods focus on formulation delivery to diseased tissues in the human body and may improve treatment safety and efficacy.

Embodiments of the present invention are directed to the treatment of hypertension, diabetes, obesity, heart failure, end-stage renal disease, digestive disease, cancers, tumors, pain, asthma and chronic obstructive pulmonary disease (COPD) by delivery of an effective amount of a formulation to diseased tissues. Such formulations include gases, vapors, liquids, solutions, emulsions, and suspensions of one or more ingredients. Methods involve controlled delivery of the formulations to lumen surfaces and tissues within the human body, resulting in modifications to those areas. Such methods can lead to denervation of nerves and nerve endings in the body lumens. The methods can also include the beneficial severing of nerves and nerve endings in order to interrupt nerve communication. Temperature may enhance the safety and efficacy of the treatment formulations. The temperature may range from −40 to 140° C., from −30 to 100° C., or from −30 to 80° C. In some embodiments, the formulation comprises one of binary, ternary or quaternary components, and may comprise more than four components. Methods of delivery include a less invasive, percutaneous approach and a non-invasive approach. Embodiments of the present invention provide a formulation and a delivery catheter, which enhances absorption and penetration into body tissues and lumen nerves and nerve endings.

In one embodiment, at least one ingredient of the formulation is chosen from water, saline, hypertonic saline, phenols, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, urea, lipiodol, surfactants, and derivatives and combinations thereof.

In one embodiment, at least one ingredient of the formulation is a gas. The gas includes one of oxygen, nitrogen, helium, argon, air, carbon dioxide, nitric oxide, vapors of organic and inorganic compounds, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, and derivatives and combinations thereof.

In one embodiment, at least one ingredient of the formulation is a surfactant. The surfactant includes PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, organic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), penta(propylene glycol), poly(propylene glycol) oligomers, a block copolymer of polyethylene glycol and polypropylene glycol, Pluronic, Pluronic 85, and derivatives and combinations thereof.

In one embodiment, the formulation includes at least an oil, a fatty acid, and/or a lipid. In some embodiments, the at least oil, fatty acid, and/or lipid in the formulation is chosen from butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines, phosphatidylglycerols, sphingolipids, prostaglandins, gangliosides, neobee, niosomes, and derivatives thereof.

In another embodiment, the formulation includes a therapeutic agent or drug for nerve denervation. The therapeutic agent includes one of sodium channel blockers, tetrodotoxins, saxitoxins, decarbamoyl saxitoxins, vanilloids, neosaxitoxins, lidocaines, conotoxins, cardiac glycosides, digoxins, glutamates, staurosporines, amlodipines, verapamils, cymarins, digitoxins, proscillaridins, quabains, veratridines, domoic acids, ethanols, oleandrins, carbamazepines, aflatoxins, guanethidines, and guanethidine sulfates. In another embodiment, the formulation includes a contrast agent for imaging nerve denervation. Such contrast agents include one of iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives, In one embodiment the formulation includes an azeotrope. An azeotrope is a mixture of two or more ingredients that cannot be altered by simple distillation. This happens because the vapor produced upon boiling has constituents proportional to those of the original mixture. Potential formulation azeotropes include ethanol/water, ethanol/water/contrast agent, ethanol/water/surfactant, ethanol/water/contrast agent/surfactant, propanol/water, isopropanol/water, butanol/water, acetic acid/water, and their combinations.

In one embodiment the formulation is in a gaseous or vapor state and includes one or more ingredients. The vapor or gas formulation can include one of oxygen, nitrogen, helium, argon, air, carbon dioxide, nitric oxide, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, and mixtures thereof. In one embodiment, the vapor formulation includes one of binary, ternary or quaternary components, and may comprise more than four components. The vapor formulation can include an azeotrope or a contrast agent, such as lipiodol or iodine, and may include a surfactant and/or a therapeutic agent. The elevated temperature of the vapor formulation may range from 0° C. to 140° C., from 15° C. to 100° C., or from 20° C. to 85° C.

In one embodiment the formulation is in a liquid state and includes one or more ingredients. The liquid formulation may include one of water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, lipiodol, methyl acetate, ethyl acetate, ethyl nitrate, isopropyl acetate, ethyl lactate, urea, surfactant, and others. The liquid formulation may include an azeotrope, contrast agent and/or a therapeutic agent. In one embodiment, the formulation may include one of binary, ternary, or quaternary components, and may also include more than four components. In some embodiments, the liquid formulation temperature may range from −40° C. to 140° C., from −30° C. to 100° C., or from −20° C. to 80° C. The liquid formulation may include a solution, a suspension, and an emulsion.

In one embodiment, the method for treatment of diseases includes inserting a delivery catheter percutaneously and/or transorally into the diseased tissues in the human body; using the catheter to infuse a therapeutic formulation into the tissues of the body, wherein the amount of the formulation delivered is effective to injure or damage the tissues, such as, for instance, by lowering blood pressure, reducing glucose level and relieving shortness of breath; optionally removing the formulation; and, lastly, withdrawing the delivery catheters from the body. The diseases for this treatment include one of hypertension, pulmonary hypertension, diabetes, obesity, heart failure, end-stage renal disease, digestive disease, cancers, tumors, pain, asthma and chronic obstructive pulmonary disease (COPD). The body lumen applicable to such a treatment include renal arteries and veins, pulmonary arteries, vascular lumens, celiac arteries, common and proper hepatic arteries, gastroduodenal arteries, right and left hepatic arteries, splenic arteries, right and left gastric arteries, nonvascular lumens, airways, the sinus, the esophagus, respiratory lumens, digestive lumens, the stomach, the duodenum, the jejunum, cancers, tumors, pain, and urological lumens. The digestive lumens applicable to such a treatment include the esophagus, the stomach, the duodenum, the jejunum, the small and large intestines, and the colon. The formulations applicable to such a treatment include gases, vapors, liquids, solutions, emulsions, and suspensions of one or more ingredients. If the formulation comprises vapors of one or more ingredients, the heat can be generated by condensation of the vapors into liquids in the tissue, If the formulation comprises liquids or solutions, the cooling or heat can be generated from formulation temperatures that fall below or exceed body temperature. The liquid formulation temperature may range from −40° C. to 140° C., from −30° C. to 100° C., or from −20° C. to 80° C. In one embodiment, the formulation temperature may equal that of room temperature. In one embodiment, the formulation temperature may range from −40° C. to −20° C. In another embodiment, the formulation temperature may range from 15° C. to 80° C. In one embodiment, the formulation temperature may equal that of body temperature. In another embodiment, the formulation temperature may range from 50° C. to 80° C. In another embodiment, the temperature of the treated tissue may be lower than the formulation temperature and higher than body temperature. The temperature of the treated tissue may range from −40° C. to 100° C., from −30° C. to 80° C., or from −20° C. to 80° C. In one embodiment, the temperature of the treated tissue may range from −40° C. to −20° C. In another embodiment, the temperature of the treated tissue may range from 15° C. to 80° C. In one embodiment, the temperature of the treated tissue may equal that of body temperature. In another embodiment, the temperature of the treated tissue may range from 50 to 80° C. The delivery catheter applicable to such a treatment includes a needle or needle-based catheter under imaged guide. The imaged guide includes one of ultrasound, X-ray, CT scan, Mill, OCT or scopes. The delivery catheter can also be balloon-based. Such balloon-based catheters can have single, double or triple balloons. The delivery catheters can also be infusion-based. The combination of a balloon and infusion catheter can also be used in the procedure. In one embodiment, the method includes flushing from a catheter distal tip like wire lumen to protect and to dilute the migrated chemical, and to prevent the runaway chemical from entering the distal portion of the untreated area; flushing from infusion catheter; flushing from endoscope; removing or withdrawing the formulations from body tissues and lumens following treatment, and flushing the target area post-treatment with saline.

It is understood that both the foregoing general description and the following detailed description are exemplary and explanatory only and are not restrictive of the present invention as claimed.

DESCRIPTION

Figure 1:
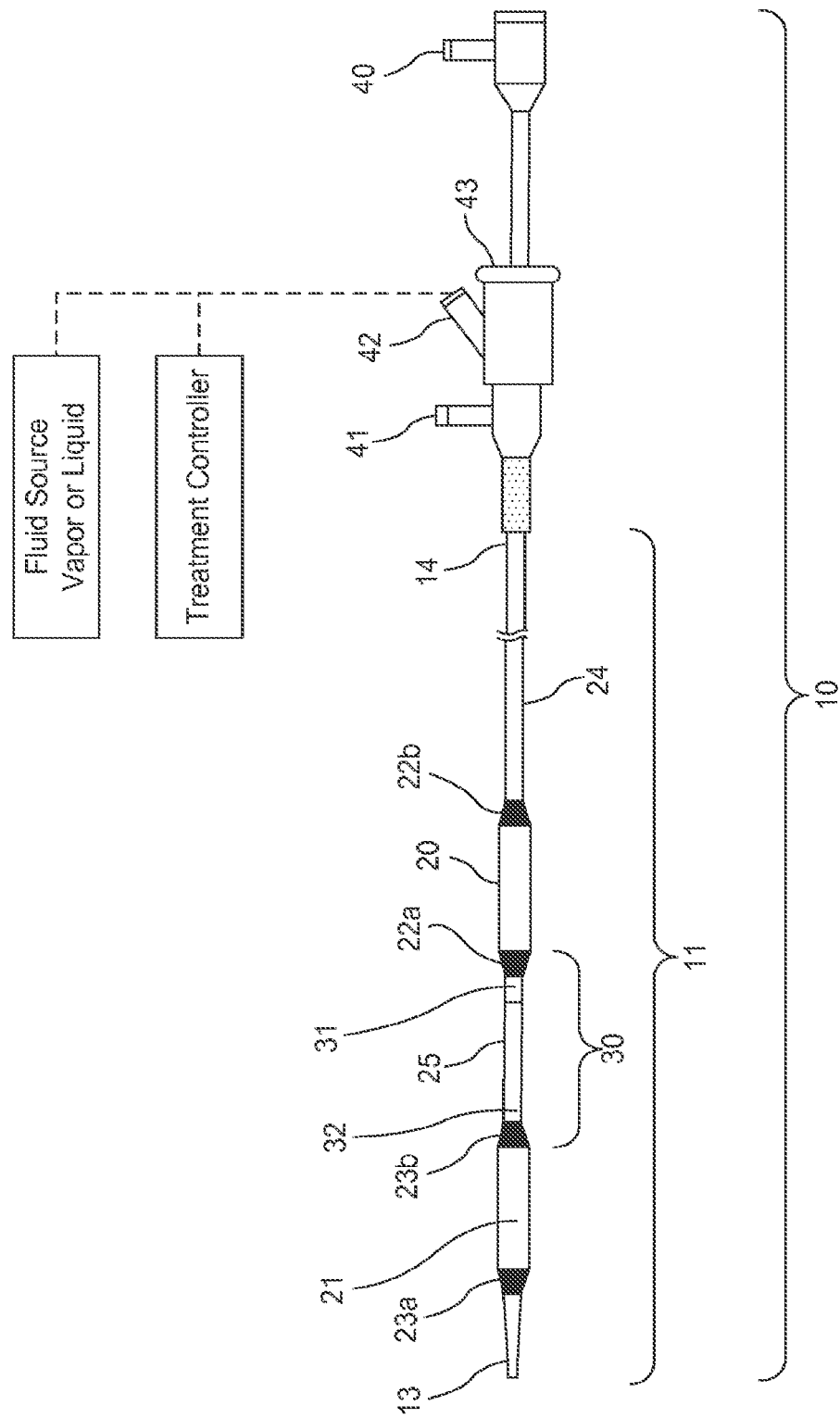
FIG. 1 is an exemplary embodiment of a perspective view of a double balloon delivery catheter according to the present invention.

Embodiments of the present invention are directed to the treatment of disease by delivery of an effective amount of formulation to target tissues in a body lumen. The disease may be one of hypertension, pulmonary hypertension, diabetes, obesity, heart failure, end-stage renal disease, digestive disease, cancers, tumors, pain, asthma or chronic obstructive pulmonary disease (COPD). The cancers include adrenal, bladder, cervical, colon, esophageal, gallbladder, kidney, liver, lung, ovarian, pancreatic, prostatic, rectal, stomach, and uterine. The formulations include gases, vapors, liquids, solutions, emulsions, and suspensions of one or more ingredients. The methods involve delivery of the formulations to lumen surfaces, tissues and nerves in the human body in order to modify such surfaces, tissues and nerves. The body lumen include a renal artery and a vein, a pulmonary artery, a vascular lumen, a celiac artery, a common hepatic artery, a proper hepatic artery, a gastroduodenal artery, a right hepatic artery, a left hepatic artery, a splenic artery, a right gastric artery, a left gastric artery, a blood vessel, a nonvascular lumen, an airway, a sinus, an esophagus, a respiratory lumen, a digestive lumen, a stomach, a duodenum, a jejunum, a cancer tissue, a tumor, and a urological lumen. The digestive lumens include the esophagus, the stomach, the duodenum, the jejunum, the small and large intestines, and the colon. The temperature may enhance the safety and efficacy of treatment formulations. The temperature may range from −40° C. to 140° C., from −30° C. to 100° C., or from −20° C. to 80° C. The temperature of the treated tissue may be different from the formulation temperature. The temperature of the treated tissue may range from −40° C. to 100° C., or from −30° C. to 80° C. The amount of formulation and energy delivered may be effective to injure, damage or eliminate diseased tissues, such as, for instance, by lowering blood pressure, shrinking tumors, relieving pain, or relieving symptoms of asthma and COPD. The energy or heat can enhance the injury/damage/elimination effect by accelerating the reaction rate between the formulation and tissues. Methods of delivery include delivery of the formulations to ablate nerves that surround the human body lumens. Such methods include removing or withdrawing the formulations from the tissue or lumen after treatment.

In one embodiment, the formulation is a single chemical or one of binary, ternary, or quaternary components, and may also include more than four components. In one embodiment, the delivery system may include less invasive percutaneous approaches or non-invasive approaches. Embodiments of the present invention include a formulation comprising one or more ingredients that enhance both surface modification of the body lumen and absorption and penetration into tissues and nerves and nerve endings of the body lumens.

In one embodiment, the ingredient of the formulation is chosen from water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, urea, lipiodol, surfactant, and derivatives and combinations thereof.

In one embodiment, the ingredient of the formulation includes a gas. The gas can be chosen from oxygen, nitrogen, helium, argon, air, carbon dioxide, nitric oxide, vapors of organic and inorganic compounds, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, and mixtures thereof.

In one embodiment, the ingredient in the formulation includes a surfactant in some embodiments, the surfactant is chosen from PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, organic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), penta(propylene glycol), poly(propylene glycol) oligomers, a block copolymer of polyethylene glycol and polypropylene glycol, Pluronic, Pluronic 85, and derivatives and combinations thereof. In some embodiments, the content of the surfactant in the formulation may range from 0.1% by weight to 80% by weight, from 0.5% by weight to 50% by weight, or from 1% by weight to 15% by weight.

In one embodiment, the formulation includes at least one of an oil, a fatty acid, and/or a lipid. The at least one of an oil, a fatty acid, and a lipid in the formulation is chosen from butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines, phosphatidylglycerols, sphingolipids, prostaglandins, gangliosides, neobee, niosomes, and derivatives thereof.

In another embodiment, the formulation includes a therapeutic agent or drug for nerve denervation and surface modification. The therapeutic agent is one of sodium channel blockers, tetrodotoxins, saxitoxins, decarbamoyl saxitoxins, vanilloids, neosaxitoxins, lidocaines, conotoxins, cardiac glycosides, digoxins, glutamates, staurosporines, amlodipines, verapamils, cymarins, digitoxins, proscillaridins, quabains, veratridines, domoic acids, ethanols, oleandrins, carbamazepines, aflatoxins, guanethidines, or guanethidine sulfates. In another embodiment, the formulation includes a contrast agent for imaging nerve denervation. Such contrast agents include iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives. The content of the contrast agent in the formulation may range from 2 to 25% by weight, or from 5 to 15% by weight.

In one embodiment, the formulation includes an azeotrope. An azeotrope is a mixture of two or more ingredients that cannot be altered by simple distillation. This happens because the vapor produced upon boiling has constituents proportional to those of the original mixture. The azeotrope is chosen from ethanol/water, ethanol/water/contrast agent, ethanol/water/surfactant, ethanol/water/contrast agent/surfactant, propanol/water, iso-propanol/water, butanol/water, and acetic acid/water.

In one embodiment, the formulation is in a gaseous or vapor state, including one or more ingredients. In one embodiment, the gas or vapor formulation includes one of oxygen, nitrogen, helium, argon, air, carbon dioxide, nitric oxide, and vapors of organic and inorganic compounds. The vapors of the organic and inorganic compounds include one of water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, and their mixtures.

In one embodiment, the vapor formulation includes at least one a contrast agent, such as lipiodol or iodine, or an azeotrope, and may also include a surfactant and/or a therapeutic agent. In one embodiment, the vapor is one of binary, ternary, or quaternary components, and may also include more than four components. The vapor formulation temperature may range from 0° C. to 140° C., from 15° C. to 100° C., or from 30° C. to 80° C.

In one embodiment, the formulation is in a liquid state, including one or more ingredients. The liquid formulation includes one of water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, lipiodol, methyl acetate, ethyl acetate, ethyl nitrate, isopropyl acetate, ethyl lactate, urea, surfactant, and others. In one embodiment, the liquid formulation includes a contrast agent and/or an azeotrope, and may also include a therapeutic agent. In one embodiment, the liquid formulation is one of binary, ternary, or quaternary components, and may also include more than four components. In one embodiment, the liquid formulation includes a solution, an emulsion, or a suspension. The liquid formulation temperature may range from −40° C. to 140° C., from −30° C. to 100° C., or from −30° C. to 80° C. In one embodiment, the formulation temperature may be room temperature. In one embodiment, the formulation temperature may range from −40° C. to −20° C. In another embodiment, the formulation temperature may range from 15 C to 80° C. In one embodiment, the formulation temperature may be equal to body temperature. In another embodiment, the formulation temperature may range from 50° C. to 80° C.

In one embodiment, the method for treatment of disease includes inserting a delivery catheter percutaneously or transorally into the body; using the catheter to infuse a formulation to diseased tissues or lumens in the body; optionally removing or withdrawing the formulation from the diseased tissue or body lumen; and, lastly, withdrawing the delivery catheters from the body. The diseases for treatment include hypertension, pulmonary hypertension, diabetes, obesity, heart failure, end-stage renal disease, digestive disease, urological disease, cancers, tumors, pain, asthma and chronic obstructive pulmonary disease (COPD). The cancers include adrenal, bladder, cervical, colon, esophageal, gallbladder, kidney, liver, lung, ovarian, pancreatic, prostatic, rectal, stomach, and uterine. The body lumen include renal arteries, vascular lumens, celiac arteries, common and proper hepatic arteries, gastroduodenal arteries, right and left hepatic arteries, splenic arteries, right and left gastric arteries, nonvascular lumens, airways, sinuses, the esophagus, respiratory lumens, digestive lumens, the stomach, the duodenum, the jejunum, and urological lumens. The digestive lumens include the esophagus, the stomach, the duodenum, the jejunum, the small and large intestines, and the colon. The formulations include gases, vapors, liquids, solutions, emulsions, and suspensions of one or more ingredients. In embodiments where the formulation includes vapors of one or more ingredients, the heat can be generated by condensation of the vapors into liquids in the tissue. In embodiments where the formulation includes liquids or solutions, cooling or heat can be generated from formulation temperatures that fall below or exceed body temperatures. The liquid formulation temperature may range from −40° C. to 140° C., from −30° G to 100° C., or from −30° C. to 80° C. In one embodiment, the temperature of the treated tissue may be different from the formulation temperature and lower or higher than body temperature. The temperature of the treated tissue may range from 15° C. to 100° C., from 20° C. to 90° C., or from 36° C. to 80° C. In another embodiment, the temperature of the treated tissue may range from −40° C. to −20° C. In some embodiments, the delivery catheter is a needle or a needle-based catheter under imaged guide. The imaged guide is one of ultrasound, X-ray, CT-scan, Mill, OCT or scopes. The delivery catheter can also be balloon- or infusion-based. Balloon-based catheters can have single, double or triple balloons. Infusion catheters can have a dumbbell balloon. Typically, there are three sections of the dumbbell infusion balloon: proximal, distal and middle. The middle section has a smaller diameter with or without infusion holes, and the proximal and the distal sections of the balloon have a larger diameter without infusion holes. The infusion is from an expandable catheter component if the middle section of a dumbbell balloon has holes (FIGS. 3A and 3B) and is defined as an expandable infusion method. The initial infusion pressure may range from 0.1 atm, to 14 atm, from 1 atm to 10 atm, or from 3 atm to 8 atm, depending upon applications. The infusion time may range from 0.1 minutes to 2 hours, from 0.5 minute to 30 minutes, or from 1 minute to 10 minutes. During the infusion time period following initial infusion pressure, the balloon pressure may be in a range from 0.1 atm to 3 atm, from 0.1 atm to 2 atm, and from 0.3 atm to 1 atm. The formulation infusion temperature may range from −40° C. to 150° C., from −30° C. to 100° C., or from −20° C. to 80° C.

In one embodiment, the infusion feature can be made from a hypotube/tube, either made of plastics or metals, which is attached to a no-hole dumbbell-type balloon catheter. The infusion is from a non-expandable catheter component when treatment formulation is delivered through holes on the hypotube/tube and the hypotube/tube is moving with the balloon towards the vessel wall; this infusion is defined as a hybrid method including the combination of non-expandable and expandable infusion methods. Typically, the hole section of the hypotube/tube is aligned along the middle section of the dumbbell balloon to control the location of formulation flow.

In another embodiment, the infusion lumen can be placed inside the catheter shaft, such as in the multi-lumen shaft for the non-expandable infusion method. In this case, holes are located on the non-expandable section between the balloons on the shaft (FIGS. 7, 8A-8B, 9A-9C). More detailed examples of the device, such as double-balloon and triple-balloon infusion catheters, are shown in the following sections.

In one embodiment, the metal hypotube can have a Bard triangle feature, which will enhance the diffusion of a formulation by creating very small holes inside the vessel wall or in the tissues. The height of the Bard triangle can range from 0.25 to 2 mm. This infusion method is a hybrid method.

In one embodiment, the formulation comprises ethanol. This formulation can be delivered to the tissues of the body lumen as vapor or liquid. The vapor or liquid formulation temperature may range from −40° C. to 150° C., from −30° C. to 100° C., or from −20° G to 80° C. The temperature of the tissue may range from −40° C. to 90° C., or from −30° C. to 80° C. In one embodiment, the formulation consists essentially of ethanol. In one embodiment, the formulation consists of ethanol.

In one embodiment, the formulation is a mixture of ethanol and water. The ethanol content can range from 10 to 100% by weight. This formulation can be delivered to the tissues of the body lumen as vapor or liquid. The vapor or liquid formulation temperature may range from −40° C. to 150° C., from −30° C. to 100° C., or from −20° C. to 80° C. The temperature of the tissue may range from −40° C. to 90° C., from −30° C. to 80° C. The ethanol/water formulation may be a positive azeotrope. The azeotrope may be 95.63% ethanol and 4.37% water by weight. Ethanol boils at 78.4° C., water boils at 100° C., and the azeotrope boils at 78.2° C., which is lower than either of its constituents. 78.2° C. is the minimum temperature at which any ethanol/water solution can boil at atmospheric pressure.

In another embodiment, the formulation is a mixture of vapors comprising water, ethanol and oxygen. In another embodiment, the formulation is a mixture of vapors comprising water, ethanol and air. In another embodiment, the formulation is a mixture of vapors comprising water, ethanol, oxygen and nitrogen. The formulations with oxygen and air are especially useful for treating asthma and COPD.

In another embodiment, the formulation is a mixture of vapors comprising water, ethanol and iodine, wherein an effective amount of the iodine vapor is included so as to be able to image the mixture of vapors in the wall of the body lumen. In another embodiment, the formulation is a mixture of liquids comprising water, ethanol and a surfactant. In another embodiment, the formulation is a mixture of liquids comprising water, ethanol and a contrast agent, wherein an effective amount of the contrast agent is included so as to be able to track the mixture in the wall of the body lumen by X-ray. The contrast agent is one of iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and derivatives thereof. The content of the contrast agent in the formulation may range from 2 to 20% by weight, or from 5 to 15% by weight.

In one embodiment, the formulation is a mixture of acetic acid and water. The acetic acid content of the formulation may range from 1 to 100% by weight, from 10 to 75% by weight, or from 20 to 50% by weight The formulation may be delivered to tissues of the body lumen as vapors or liquid. The vapor or liquid formulation temperature may range from −40° C. to 100° C., from −30° C. to 100° C., or from −30° C. to 80° C. The temperature of the tissue may range from −30° C. to 80° C., from 60° C. to 80° C. or from −30° C. to −20° C. The temperature of the tissue may range from −40° C. to 0° C., or from −30° C. to −20° C. The acetic acid content in the formulation may range from 2% by weight to 75% by weight, or from 10% by weight to 80% by weight.

In another embodiment, the formulation is a mixture of liquids comprising ethanol and lipiodol (LIPIODOL ULTRA-FLUIDE), wherein an effective amount of lipiodol is included so as to be able to image the mixture of vapors in the wall of the body lumen and to also injure the target nerve tissue. The lipiodol content of the formulation may range from 10% by weight to 80% by weight, from 15% by weight to 75% by weight, or from 20% by weight to 50% by weight. In another embodiment, the formulation is a mixture of liquids comprising water and lipiodol. The lipiodol content of the formulation may range from 10% by weight to 80% by weight, from 15% by weight to 75% by weight, or from 20% by weight to 50% by weight. In another embodiment, the formulation is a mixture of liquids comprising acetic acid and lipiodol. The content of lipiodol in the formulation may range from 10% by weight to 80% by weight, from 15% by weight to 75% by weight, or from 20% by weight to 50% by weight.

In one embodiment, a delivery catheter is used in the invention to infuse the formulation to the tissues of the human body. The delivery catheter is a needle or needle based catheter under X-ray or ultrasound-imaged guide. The delivery catheter can be balloon-based with single, double or triple balloons. The delivery catheters can also be infusion-based. The combination of balloon and infusion catheter can also be used in the procedure. The balloon in the infusion system should be able to confine the formulation within the balloon well and appropriately control the formulation volume.

In one embodiment, a dilating balloon catheter is used in the invention for delivery of active materials to a target location in the body lumen of a patient, the dilating balloon catheter comprising a proximal end, a distal end, a wire, a lumen, a balloon inflation lumen, a formulation infusion lumen and/or a vacuum lumen, an expandable balloon section and a non-expandable shaft section, wherein the expandable balloon section comprises at least one section and the non-expandable shaft section comprises at least one section, at least one first section of the expandable section and/or the non-expandable section having a plurality of voids, wherein the voids are micro-holes, and at least one second section of the expandable section and/or the non-expandable shaft section having no voids. The expandable section or non-expandable section of the dilating balloon catheter has at least one void that allows the formulation to penetrate into the wall of the body lumen at a pressure higher than that of the body lumen. The expandable section or non-expandable section has no void that allows the balloon to dilate the body lumen at a pressure higher than that of the body lumen.

As shown in FIG. 1, a delivery catheter 10 has an elongated shaft 11 with at least one inner lumen, a distal end 13, and a proximal end 14. At the distal end 13 are proximal 20 and distal 21 lumen-conforming balloons. In any configuration, the tubing of the catheter shaft 11 may be extruded from plastic materials, e.g. thermoplastics, polyimides, polyetherimides, polyethylenes, polyurethanes, polyesters, polyamides, Pebax, nylons, fluorinated polyurethanes, polyether ether ketones, polysulfones, or the like, The catheter shaft 11 may be extruded or formed with a variety of lumen cross-sections, including circular or elliptic lumens. Further, as shown in FIG. 1, the catheter 10 may be equipped with a distal balloon inflation port 40 for inflation of the distal balloon 21 and a proximal balloon inflation port 41 for inflation of the proximal balloon 20, rendering the proximal 20 and distal 21 balloons separately inflatable. The lumen-conforming balloons are balloons that can be inflated at a pressure less than that needed to deform the lumen wall. The balloon material is selected to be flexible and usable at high temperatures, such that the balloon, when inflated, is compliant. In one embodiment, the balloon material is one of polyamides, nylons, Pebax, polyesters, polyethylene teraphthalates or their copolymers. The diameter of the balloons can range from about 2 millimeters to about 40 millimeters, depending on the diameter of the treatment site. In one embodiment, the diameter of each balloon is about 2 millimeters ("mm"). Alternatively, the diameter of each balloon is about 3 millimeters, or, alternatively, about 4 millimeters, or, alternatively, about 5 millimeters, or, alternatively, about 6 millimeters, or, alternatively, about 7 millimeters, or, alternatively, about 8 millimeters, or, alternatively, about 9 millimeters, or, alternatively, about 10 millimeters, or, alternatively, about 12 millimeters, or, alternatively, about 15 millimeters, or, alternatively, about 20 millimeters, or, alternatively, about 25 millimeters, or, alternatively, about 30 millimeters, or, alternatively, about 35 millimeters, or, alternatively, about 40 millimeters In one embodiment, at least one marker band 22b is located proximally to the proximal balloon 20 and at least one marker band 23a is located distally to the distal balloon 21. The balloon catheter may be a rapid exchange or over-the-wire catheter made of any suitable biocompatible material. Marker bands can also be positioned on the other ends of balloons (22a and 23b). 25 is the segment in between balloons 21 and 21 with at least one infusion hole. 30 is the non-expandable section; 31 and 32 are micro-voids or holes; 24 is the shaft proximal to the balloon section. 40 and 41 are the ports for balloon inflation for the distal and proximal balloons, respectively. 42 is the infusion port for chemical formulation.

The material of balloon 20 and 21 is made of one of polyesters, polyamides, nylon 12, nylon 11, polyamide 12, block copolymers of polyether and polyamide, Pebax, polyurethanes, or block copolymers of polyether and polyester. The diameter of balloon 21 is equal to or less than that of balloon 20.

Figure 2:
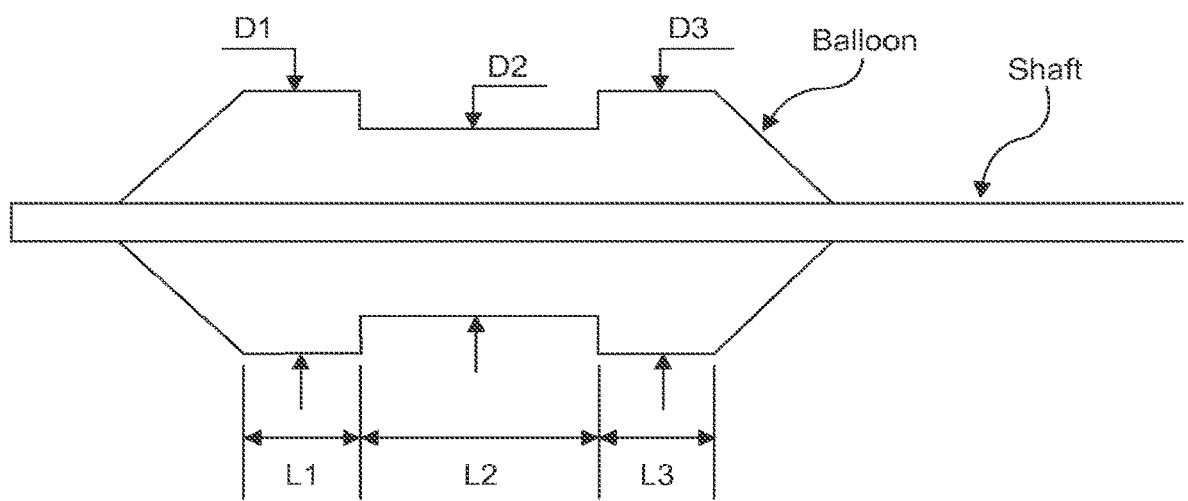
FIG. 2 is an embodiment of a side view of a distal portion of an expanded dumbbell balloon.

In one embodiment, a schematic dumbbell balloon is shown in FIG. 2. In an expanded state, its middle diameter D2 is smaller than both of its end diameters D1 and D3. D1 and D3 can be equal in length or different. Each diameter section has its own length, L1, L2 and L3, respectively. For simple illustration, a dumbbell-type balloon is used for the descriptions below. However, other similar-type balloons like a multi-groove balloon, in which the grooves are located in the middle section of the balloon, can achieve the same feature/function. The design of the dumbbell-type balloon shape allows for the balloon to have better infusion volume control and formulation location control inside the targeted vessel because the two larger ends block the formulation flow path. In one embodiment, the delivered formulation will be confined mostly to the middle section of the smaller diameter, as shown in FIG. 2. A controlled treatment dosage is required for procedural safety, which means that the diameter ratio between the larger and smaller diameters on the dumbbell balloon is determined by clinical dosing needs. To define the diameter combination on the dumbbell balloon, the volume per surface area is used, and is calculated from the volume gap (unoccupied space over small diameter section) between the two larger diameter ends relative to the smaller diameter middle section. The equation of the ratio calculation is:

$$\text{Volume/Surface area} = (D1^2 - D2^2) \div (4 * D1) \qquad \text{Equation 1}$$

Where D1 is the diameter of the larger diameter balloon portion and D2 is the diameter of the smaller diameter balloon portion.

The ratio of volume/surface area can range from 0.1 mm to 10 mm, from 0.2 mm to 5 mm, or from 0.3 mm to 2 mm. The dose of chemical agent can, thereby, be constant and independent of balloon or vessel size. The value of the ratio is determined by clinical treatment needs (dosing requirements). The dumbbell balloon or multi-groove balloon can be made from a secondary heat-shrinking process involving a regular cylindrical balloon or by direct molding into form. The balloon body diameter difference between the larger diameter ends and the middle smaller diameter section is determined by a pre-defined value of volume/surface area ratio, which is calculated using Equation 1. For example, for the combination of 6 mm and 8 mm balloons, the calculated volume/surface area ratio would be 0.88 mm.

Overall balloon body diameter and length can range from 2 to 40 mm and 10 to 100 mm, respectively. Conventional balloon cone angle or shape is acceptable for the applications, however, round or radius cone shape is preferred.

Any balloon materials that are compatible with the formulations can be used for balloon making, such as polyethylenes, polyolefin elastomers, natural rubbers, polyesters like PET and PBT and their block copolymers including thermoplastic elastomers like Hytrel, and polyamides like nylon 12 and nylon 11 and their block copolymers including thermoplastic elastomers like Pebax.

Figure 3A:
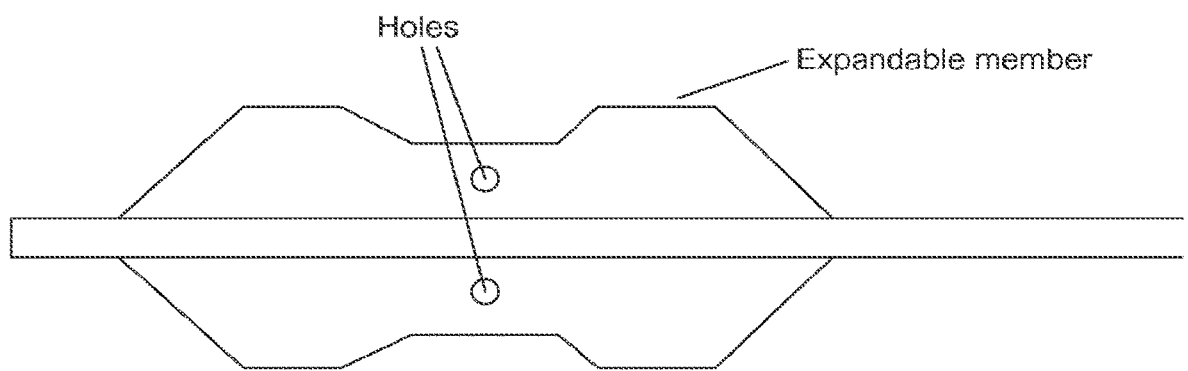
FIG. 3A is an embodiment of a side view of an infusion balloon with holes on the balloon wall for chemical agent delivery.
Figure 3B:
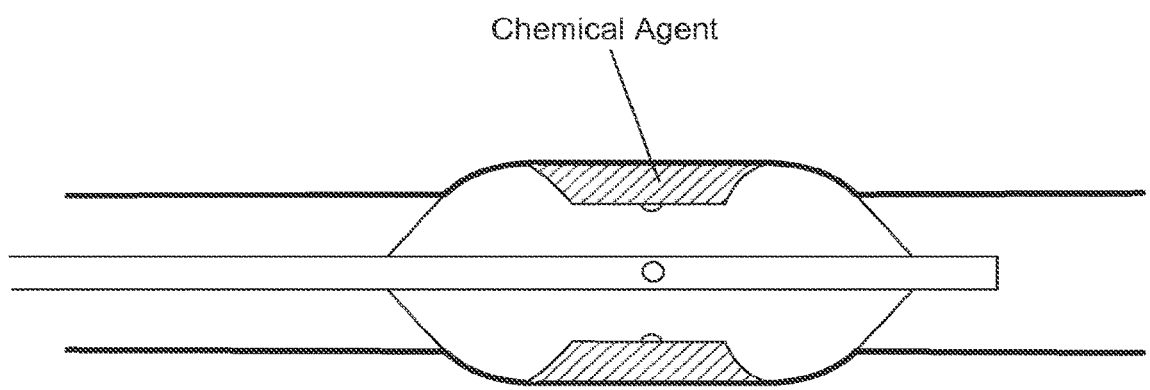
FIG. 3B is an embodiment of a side view of a chemical agent delivery system positioned in a body lumen with an expanded balloon, the chemical agent being confined mostly in between two large diameter segments.

In one embodiment, a schematic view of a dumbbell balloon infusion catheter is shown in FIG. 3A, with 4 holes arranged 90 degrees apart in the middle smaller diameter balloon section, which is modified from FIG. 2 with tapered transitions between different diameters. The liquid formulation may be delivered from the balloon inflation lumen through the holes on the balloon; this is an expandable infusion method. In this example, the formulation functions in two roles: inflating the balloon and serving as a treatment agent. FIG. 3B is a schematic view of an infusion balloon catheter inflated and positioned inside a vessel. The majority of the delivered treatment formulation is confined to the space created by the smaller balloon body and two larger balloon shoulders within the vessel wall.

To enhance the diffusion distance of the chemical treatment agent, a ratio of balloon outer diameter (OD) to vessel interior diameter (ID) that is larger than one, in which the vessel is over dilated at a specific controlled level may be used. The ratio can range from 1.01 to 10, 1.10 to 5, or from 1.20 to 1.35.

The micro holes on the balloon for delivering the chemical agent can be created by a micro-punching or drilling process directly on the balloon body wall. The suitable hole size can range from 5 microns to 500 microns, or from 20 microns to 250 microns on the balloon wall. These values appropriately consider the balance between balloon inflation, infusion rate and formulation flow control. If the hole size is too large, the formulation volume may not be controllable due to over flow. Geometrically, the holes are typically arranged in the middle section of the small diameter area; however, they can be placed in a different way or pattern on the balloon, for purposes of delivering formulation. The holes on the balloon may also be arranged along the circumference of the balloon body wall at the center of the smaller diameter section. The number of holes can range from 2 to 10 or more and the size of holes can range from 25 microns to 100 microns.

The dumbbell balloon in FIG. 3A can be considered as one groove balloon with four evenly distributed holes circumferentially, the balloon embodiment above also including multiple grooves on the balloon and each groove having its own group of holes for infusion. For example, a three-groove balloon could be made from an 80 mm long length balloon, and the infused agent could be confined within each groove. The clinical outcome of a multi-groove balloon would be the same as that of the regular dumbbell balloon shown in FIG. 3A, if their respective volume/surface area ratios were equal. FIG. 3A is a device for an expandable infusion method.

Figure 4A:
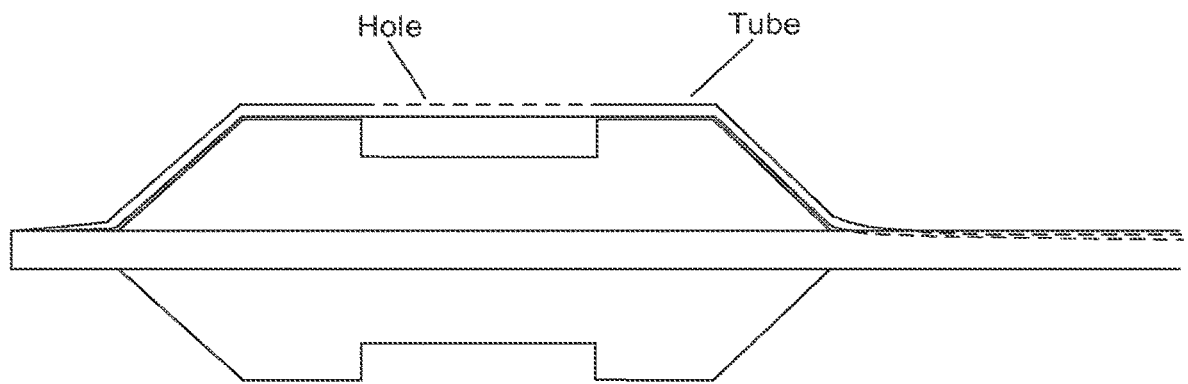
FIG. 4A is an embodiment of a side view of an infusion device with a chemical agent delivery tube attached to a balloon.
Figure 4B:
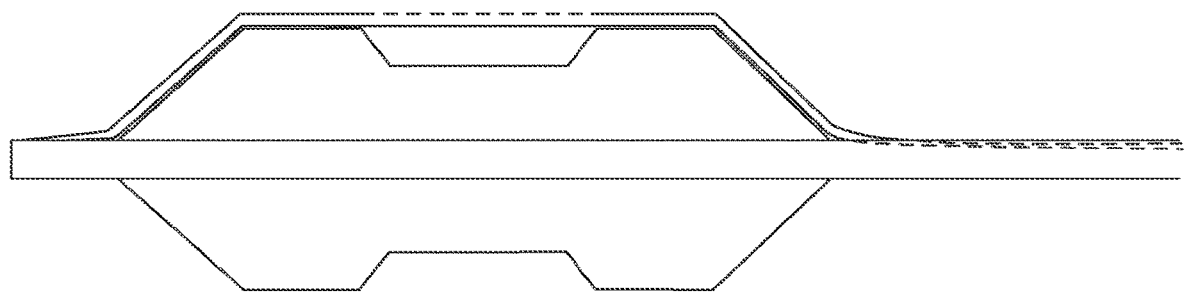
FIG. 4B is an embodiment of a side view of a dumbbell balloon infusion device with a tapered transition from larger to smaller diameter, and a chemical agent delivery tube attached.

In another embodiment, as shown in FIGS. 4A-4B, the chemical agent is delivered through a thin tube attached to the catheter at a distal and proximal balloon. In this example, a dumbbell balloon catheter without holes on the balloon is used for the infusion system. FIGS. 4A-4B are devices for a hybrid infusion method. The formulation delivery tube has multiple holes located within the balloon section of the smaller diameter. The hole size on the tube can range from 25 microns to 1 mm. The number of holes varies depending on the length of the smaller diameter balloon section. A distance between holes can range from 2 mm to 5 mm.

Due to the incorporation of the infusion tube in the embodiments shown in FIGS. 4A-4B, the balloon inflation and formulation infusion occur through separate, independent procedures. The balloon, for instance, is first inflated to a predetermined pressure; the effective volume of the chemical agent is next delivered through the tube to the treatment site while the remainder of the formulation is confined to the middle section of the smaller balloon diameter area. The infusion tube used on the catheter can be made from thermal plastics like polyethylene, nylons or Pebax, or metals or metal alloys like stainless steel or nitinol, or nitinol hypotube for its super elastic property.

Figure 15:
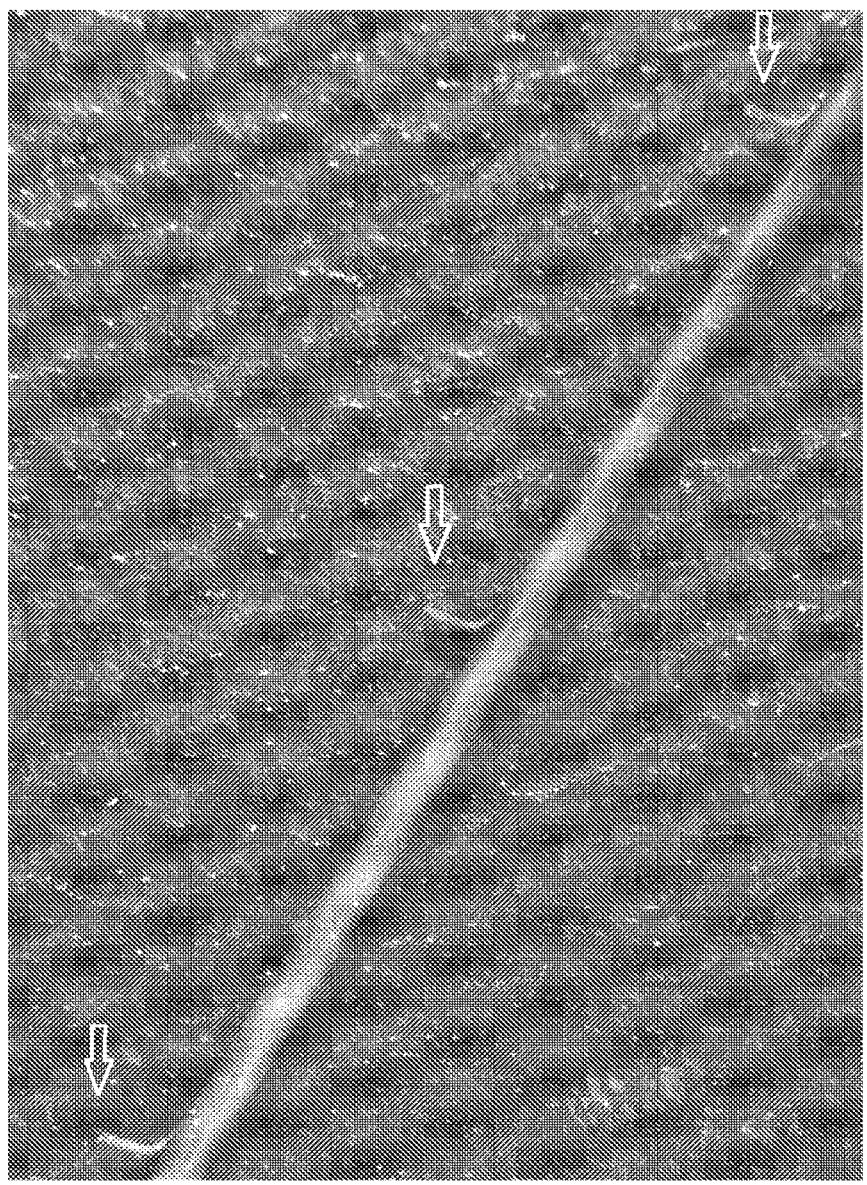
FIG. 15 is an embodiment of a metal infusion tube with Bard triangle features (as shown by white arrows).

An advantage of using metal or metal alloy tubing over plastic tubing is the presence of additional features for formulation delivery. For example, the Bard triangle feature can be added to a metal tube (FIG. 15). The sharp tip of the Bard triangle would serve to pinch into the tissue wall when the balloon is inflated against the vessel wall. Compared to the round hole version, this delivery system would enable deeper diffusion of the chemical agent into the vessel tissue in part due to the piercing of the tissue. If a deeper diffusion over a wider vessel wall area is needed, the balloon can be inflated and deflated several times and rotated after each inflation/deflation cycle. This would result in additional punctured holes on the vessel wall and would enable the formulation to diffuse through deeper and faster. The height of the Bard triangle can range from 0.25 mm to 2 mm, or from 0.5 mm to 1 mm.

Figure 5A:
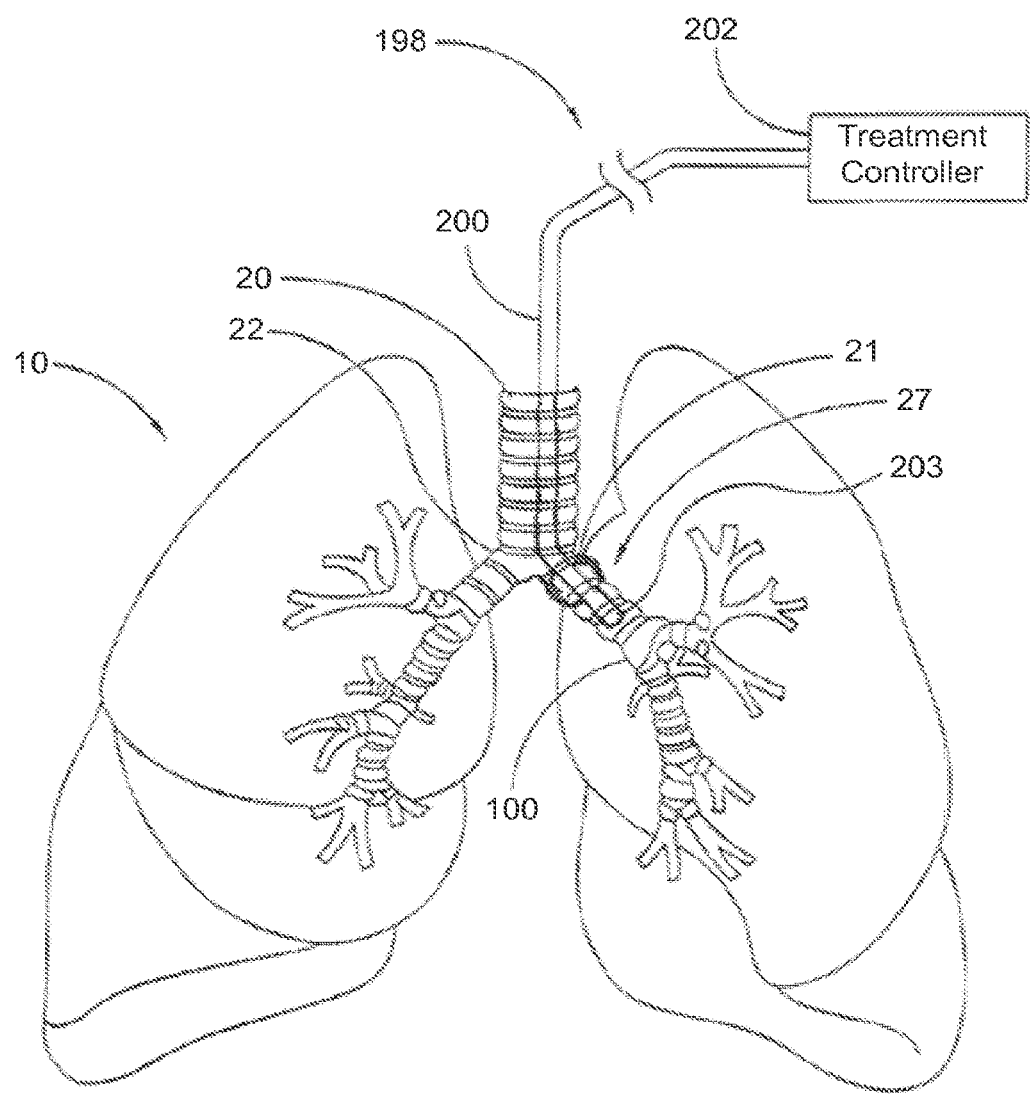
FIG. 5A is an embodiment demonstrating formulation infusion to an airway using a single balloon delivery catheter.
Figure 5B:
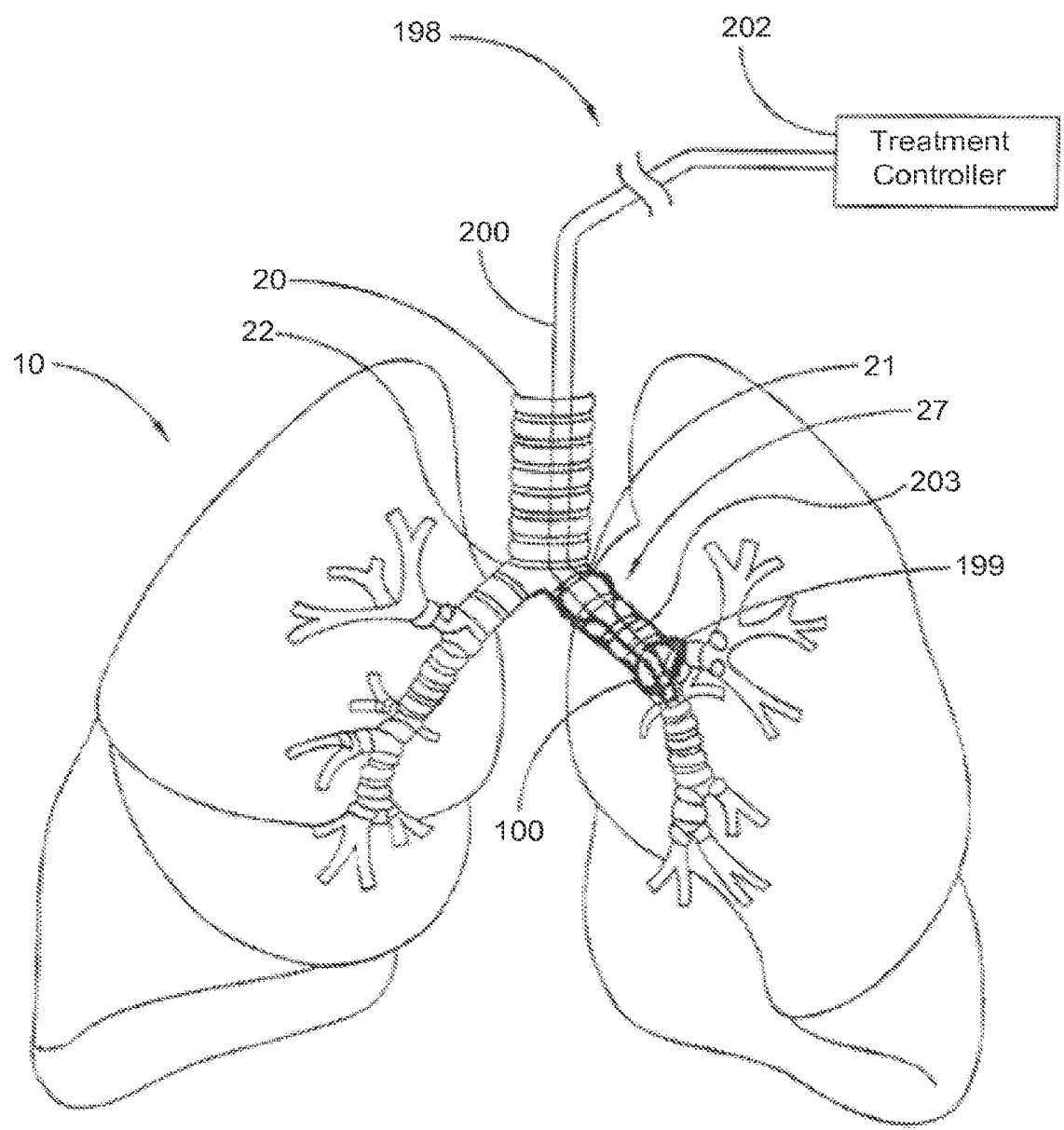
FIG. 5B is an embodiment demonstrating formulation infusion to an airway using a double balloon delivery catheter.

In one embodiment, a schematic view of a balloon delivery catheter positioned within the left main bronchus for treatment of asthma and COPD is shown in FIGS. 5A and 5B. The delivery catheter 198 of FIGS. 5A and 5B can treat airways that are distal to the main bronchi 21 and 22. For example, the delivery catheter 198 can be positioned in various airways in segments of lungs to affect remote distal portions of the bronchial tree 27. The delivery system 198 can be navigated through tortuous airways to perform a wide range of procedures, such as, for example, denervation of a portion of a lobe, an entire lobe, multiple lobes, or one or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat a lobe. Based on the effectiveness of the treatment, the physician can concurrently or sequentially treat additional lobe(s). In this manner, different isolated regions of the bronchial tree can be treated.

The delivery catheter 198 can also be used in segmental or sub-segmental bronchi. Each segmental bronchus may be treated by delivering the formulation to a single treatment site along the segmental bronchus. For example, the formulation can be delivered to each segmental bronchus of the right lung. In some procedures, one or two applications of the formulation can treat most of or the entire right lung. Depending on the anatomical structure of the bronchial tree, segmental bronchi can often be denervated using one or two applications.

The delivery catheter 198 can affect nerve tissue while maintaining the function of other tissues or anatomical features, such as the mucous glands, cilia, smooth muscle, body lumens (e.g., blood vessels), and the like. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, the delivery catheter 198 is capable of denervating a portion of an airway of the bronchial tree 27 to attenuate one or more nervous system signals transmitted by nerve tissue. Denervating can include severing the nerve tissue of a section of a nerve trunk to prevent signals from traveling through that specific area to more distal locations along the bronchial tree. If a plurality of nerve trunks extends along an airway, each nerve trunk can be severed. As such, the nerve supply along a section of the bronchial tree can be cut off. When the signals are cut off, the distal airway smooth muscle relaxes, leading to airway dilation. This airway dilation reduces airflow resistance so as to increase gas exchange in the lungs, thereby alleviating, or eliminating one or more clinical manifestations, such as breathlessness, wheezing, chest tightness, and the like. Tissue surrounding or adjacent to the targeted nerve tissue may be affected but not permanently severed. In some embodiments, for example, the bronchial blood vessels along the treated airway can deliver a similar amount of blood to the bronchial wall tissues, and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not injured to a significant extent. For example, a relatively small section of smooth muscle in an airway wall which does not appreciably impact respiratory function may be reversibly altered. If the formulation is employed at a regulated temperature to injure nerve tissue outside of the airways, that formulation will not reach a significant portion of the non-targeted smooth muscle tissue.

The delivery system 198 of FIGS. 5A and 5B includes a treatment controller 202 and an intraluminal elongate assembly 200 connected to the controller 202. The elongate assembly 200 can be inserted into the trachea 20 and navigated into and through the bronchial tree 27 with or without utilizing a delivery assembly. The elongate assembly 200 includes a distal tip 203 capable of selectively affecting tissue.

The controller 202 of FIG. 5A can include one or more processors, microprocessors, digital signal processors (DSPs), field programmable gate arrays (FPGA), application-specific integrated circuits (ASICs), memory devices, buses, power sources, pumps, formulation resources, vapor resources, liquid resources, contrast resources, vapor generators, desired temperature formulation generators, and the like.

The distal tip 203 of FIGS. 5A-5B can target various sites in the lungs 10, including, without limitation, nerve tissue, fibrous tissue, diseased or abnormal tissue, muscle tissue, blood, blood vessels, and various anatomical features (e.g., membranes, glands, cilia, and the like).

Figure 5C:
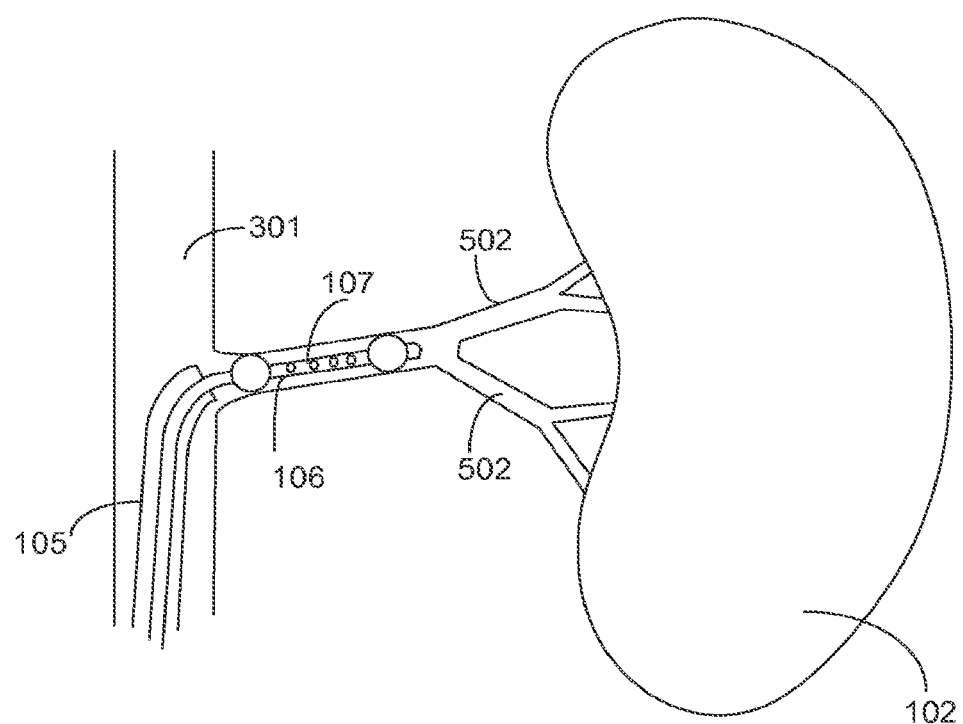
FIG. 5C is an embodiment demonstrating formulation infusion to a renal artery using a double balloon delivery catheter.

In one embodiment, a schematic view of a double balloon delivery catheter positioned within a renal artery is shown in FIG. 5C. The balloon catheter 107 of FIG. 5C can treat hypertension. The formulation is infused to the wall of the renal arteries adjacent to the renal nerves for denervation. Some of the elements of the renal vascular system are omitted in FIG. 5C. In FIG. 5C, 102 is the kidney, 105 is the guiding catheter, 106 is main renal artery, 107 is balloon catheter, 301 is abdominal aorta, and 502 extra-renal artery.

In one embodiment, the method for treatment of hypertension includes inserting a delivery catheter percutaneously into the renal artery and/or extra-renal arteries adjacent to the nerves and nerve endings; using the delivery catheter to infuse the formulation described above to the tissue of the body lumen adjacent to the nerves, wherein the amount of the formulation delivered is effective to injure the nerves and nerve endings, such as, for instance, by lowering blood pressure; and, lastly, withdrawing the delivery catheter from the body lumen.

In one embodiment, a balloon infusion catheter, for example as shown in FIGS. 3A-3B, 4A-4B, 7, 8A-8B, and 9A-9C, can be used for hypertension treatment. Examples of the pre-clinical trials with the embodiments are described below.

In one example, a porcine animal weighing 47 kg was anesthetized with isoflurane, and one side of its renal artery was ablated with ethanol using a balloon catheter while the contralateral renal artery served as a control. Using a standard renal access procedure, the balloon infusion catheters were placed into the targeted renal arteries of the main and extra-renal branches in sequence over a guide wire. Upon reaching the targeted ablation site, the balloon was inflated and absolute ethanol-mediated renal arterial chemical ablation took place via the expandable infusion method. The balloon diameter was determined according to renal angiograms, and a total of four catheters were employed. During the ablation treatment, the balloons were rapidly inflated up to 6 to 8 atm with ethanol first, then ramped down to 0.5 to 1 atm and maintained at the lower pressure for about 60 seconds. By the end of the treatment time, the balloon was deflated and withdrawn, or placed into another artery site if required for the next treatment.

For a better clinical outcome, the balloon outer diameter (OD, the larger diameter section) and the arterial inner diameter (ID) may exist in a certain ratio. A slightly over-sized balloon OD to vessel ID can be used, such as Balloon OD/Vessel ID=1.10 to 1.40; or =1.20 to 1.35.

Post-ablation renal angiograms were obtained to determine whether vessel spams, stenosis, or other abnormalities occurred. There were no significant renal arterial spasms during and after the balloon infusion treatment.

Figure 12:
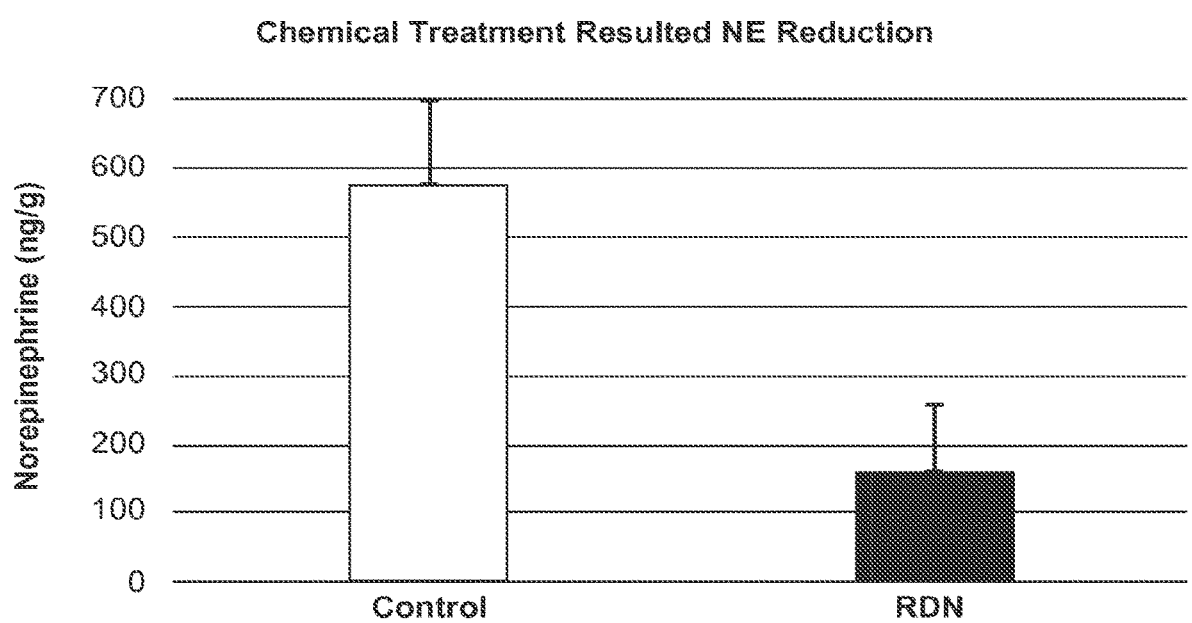
FIG. 12 is a bar graph demonstrating norepinephrine (NE) reduction following renal denervation in ethanol- vs. control-treated groups.

The animal was euthanized two weeks after treatment, and renal tissue samples were obtained from the cranial, middle, and caudal of the renal cortex to determine the renal tissue norepinephrine (NE) content using known HPLC methods. Norepinephrine is a neurotransmitter whose levels serve as a standard measurement for renal denervation. Renal arteries and surrounding tissues were collected for histopathologic evaluation as well. Ethanol ablation of the renal artery resulted in a 72% reduction in renal norepinephrine reduction (NE content: control: 570 ng/g; renal denervated, i.e. RDN: 160 ng/g), as shown in FIG. 12.

Figure 16:
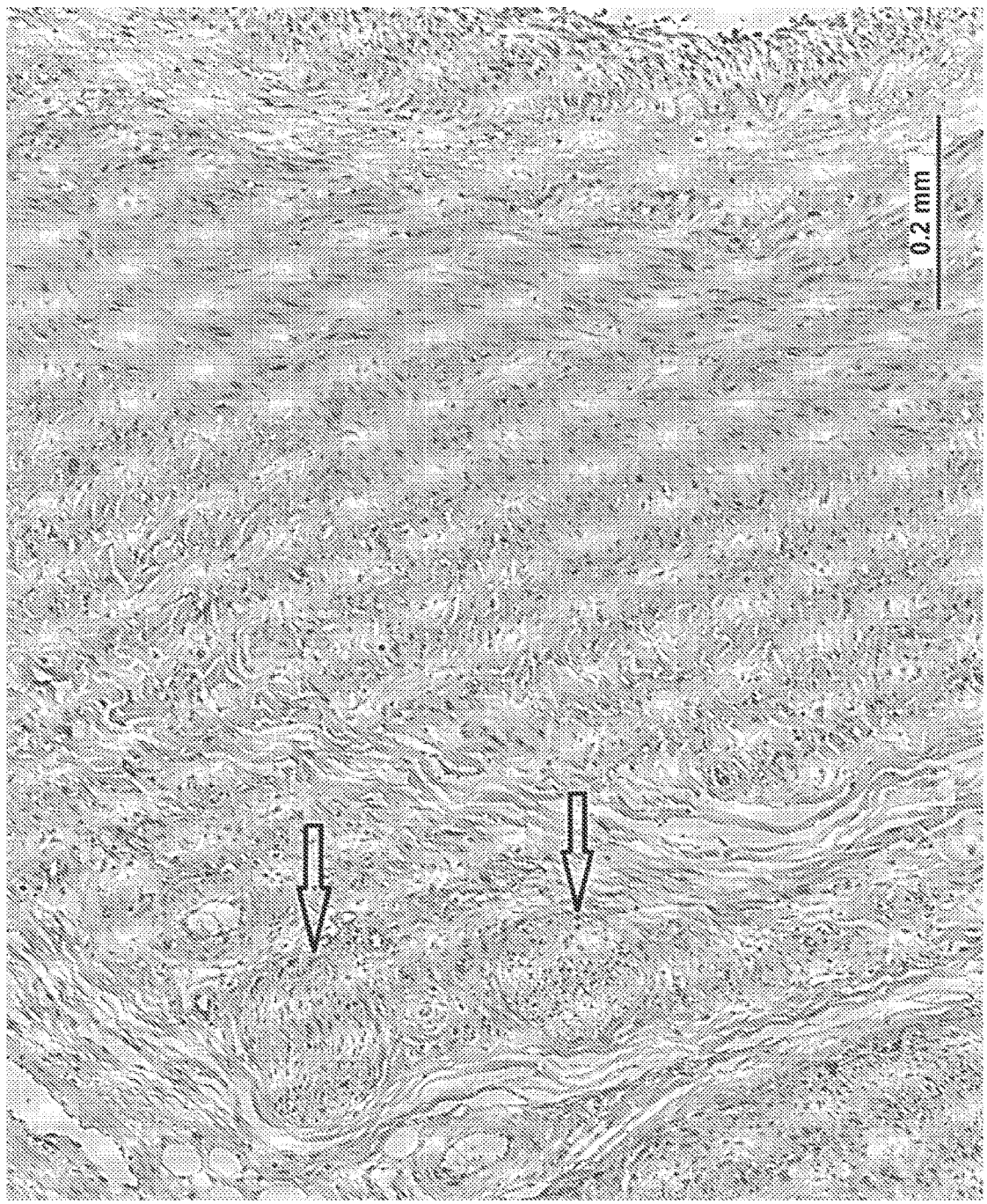
FIG. 16 is a histopathologic image demonstrating severed renal nerves (as shown by black arrows) following ethanol treatment.

Not only was the NE content reduced after ethanol ablation, but histopathologic evaluation also demonstrated renal nerve injury, as shown in FIG. 16, where nerves are pictured (black arrows) surrounded by mild fibrosis within the outer margins of the tunica adventitia.

To confirm results from the above study, a second study was conducted. The same infusion device and same study period (2-week chronic study) as described above were used in this confirmation study.

Six porcine animals weighing 44 to 56 kg were divided into three treatment sub-groups with two treated in the main renal artery, two treated in the extra-renal branches, and two treated in both the main renal artery and the extra-renal branches. Again, for each animal, one side of the renal arterial vessel(s) was (were) treated while the contralateral served as a control. A standard renal access procedure was performed.

During the treatment, balloon size was determined according to the balloon OD/artery ID ratio that range from 1.20 to 1.35. These values provided for better treatment effectiveness and minimal vessel injury by regulating over-dilatation. The inflation pressure used in this study during the rapid inflation cycle was 10 to 12 atm; the pressure was then ramped down to 0.5 to 1 atm, and the treatment was maintained at the low pressure for 2 minutes at the main renal artery site and 1 minute in the extra-renal branch arteries. Renal angiograms showed no significant renal arterial spasms during and after balloon infusion treatment in all of six porcine animals of this study.

Renal arterial ethanol ablation of the main renal artery alone resulted in an average norepinephrine (NE) reduction of about 40%. Extra-renal arterial branches ethanol ablation resulted in about an 80% norepinephrine reduction. Chemical ablation of the main renal artery and the extra-renal arterial branches collectively resulted in more than a 90% norepinephrine content reduction; cranial cortex norepinephrine reduction: 93.81%, 94.07%, 94.43%, middle cortex tissue norepinephrine reduction: 91.98%, 92.19%, 93.20%, caudal cortex tissue norepinephrine reduction: 73.27%, 31.80%, 47.06%. This study demonstrated that both the quality of the balloon and degree of renal arterial tissue contact during treatment contribute to high efficacy.

In addition to the reduction in NE, histopathologic evaluation demonstrated renal nerve injury (as shown in FIG. 16), depicting both large caliber perivascular nerves surrounded by fibrosis and inflammation and multi-focal degenerate and/or necrotic tissues. Circumferential effects were also observed. Overall, an average renal nerve injury value of 50% in the treated renal arteries was estimated.

Figure 6:
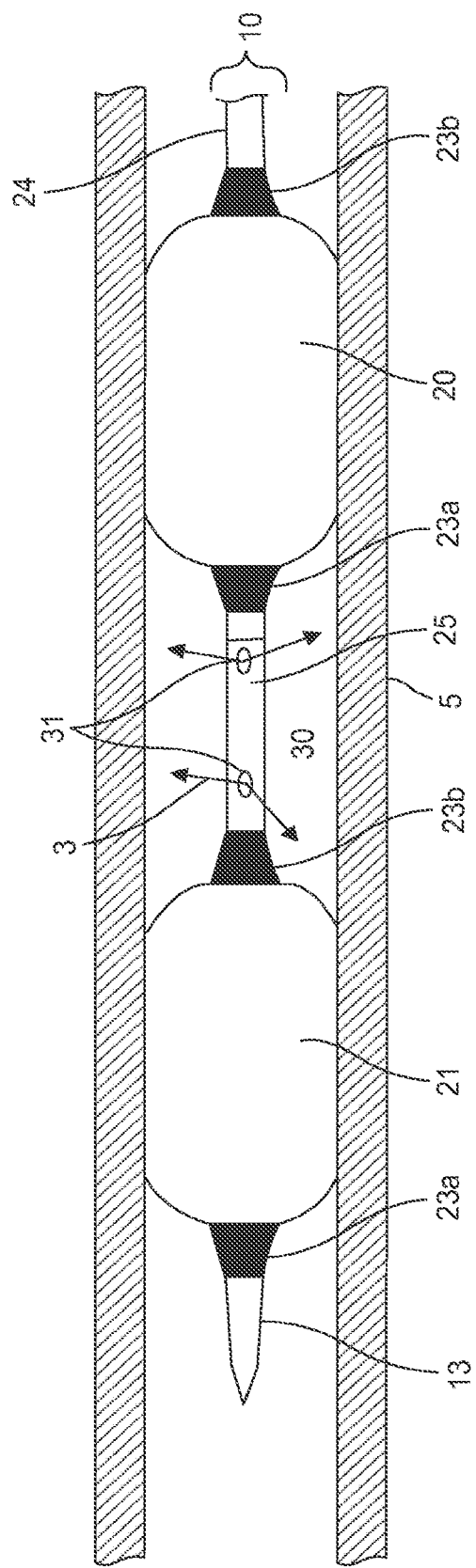
FIG. 6 is an embodiment of a partial cross-sectional view of a double balloon delivery catheter in a body lumen.

In one embodiment, the catheter 10 (in FIG. 1) disclosed herein helps regulate formulation flow and treatment dose throughout the treatment window 30, as shown in FIG. 6. Balloons can be inflated through their inflation lumen. The position, diameter, number and frequency of lateral apertures 31 results in the homogeneous filling of the treatment window 30. FIG. 6 depicts a catheter positioned in a body lumen 5 having two lateral apertures 31 located within the treatment window 30 for delivery of the therapeutic agent 3. Catheter tip 13, mark bands 23a and 23b, expandable balloons 20 and 21 are shown in FIG. 6. The lateral apertures 31, as shown in FIG. 6, are in fluid communication with the inner lumen 25. Lateral apertures 31 located within the treatment window 30 can be in communication with either the outer 24 or inner 25 lumen such that the formulation is delivered homogeneously to the treatment window 30.

Figure 7:
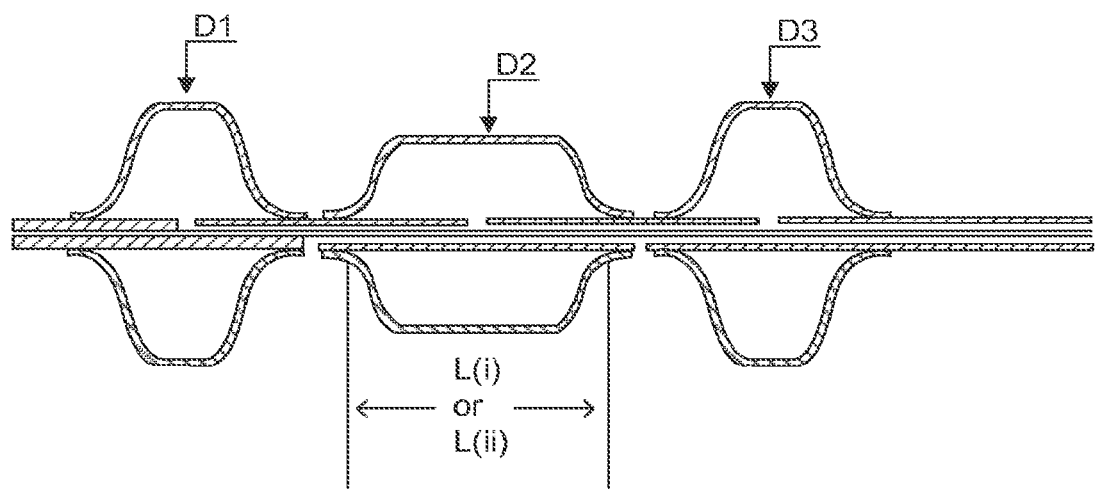
FIG. 7 is an embodiment of a partial cross-sectional view of a tri-balloon on a multi-lumen shaft with an inflation lumen and an agent delivery lumen.

In one embodiment, a cross-sectional view of the distal portion of the tri-balloon infusion catheter is depicted, as shown in FIG. 7. This infusion device can provide homogeneous filling at the treatment site. The balloons in FIG. 7 are shown in an expanded state with two larger diameter balloons, D1 and D3, at distal and proximal ends, and one smaller diameter balloon (D2) in the middle. The combination of balloon diameters is determined by Equation 1 using a pre-defined ratio value according to clinical dose requirement. The combination of balloon lengths depends on targeted vessel length and tortuousness.

One of the designs is for a four-lumen shaft that serves as an infusion catheter. The four lumens can be assigned for wire (1), balloon inflation (1) and chemical treatment (2), for example, as shown in FIG. 1. Alternatively, a catheter can be designed to have more lumens to accommodate more inflation lumens, where each balloon can be inflated independently.

Chemical treatment ports are located between the balloons on the shaft. The formulation infusion holes are located on the non-expandable shaft section between the expandable balloon sections. During treatment, the formulation can be discharged between the balloons through the infusion hole to fill in the space created by the smaller diameter balloon. This is a non-expandable infusion method.

In one embodiment, optionally, the residual of the chemical agent/formulation may be retrieved by vacuum technique on one of the infusion holes following treatment. In this case, at least two treatment lumens may be used: one for infusion and the other for vacuum. The formulation infusion and vacuum holes are located on the non-expandable shaft section between the expandable balloon sections.

In addition to the withdrawal of excess treatment agent, left-over agent can also be diluted with saline or water to an ineffective concentration. Flushing with saline or water can be performed using a catheter wire lumen, or one of the infusion lumens, or by other means. The method of use depends upon the site of protection or treatment. If the distal portion of vessels requires protection from the chemical treatment, flushing can be performed via wire lumen.

Figure 8A:
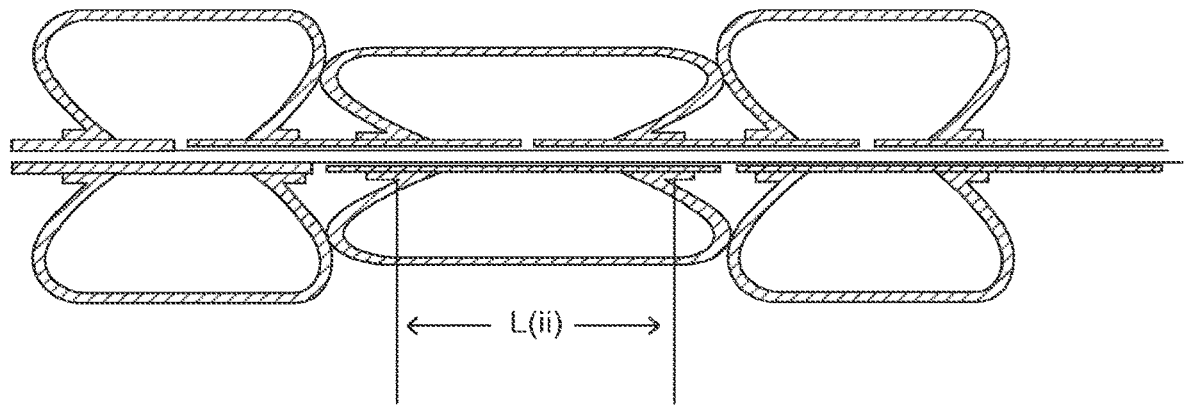
FIG. 8A is an embodiment of a partial cross-sectional view of a tri-balloon-combined infusion device with a reduced unoccupied space between two larger diameter balloons in an expanded state.

In one embodiment, as shown in FIG. 8A, a new unconventional balloon attachment method can be applied. The new method includes placing the balloon waists inside balloon cones or bodies; this serves to overcome the extra unwanted space which surrounds the smaller diameter balloon and is created by the balloon waist length and cone length, as shown in FIG. 7. Extra space confers no benefit for chemical treatment and may lead to overdose due to an inability to control therapeutic volume. The formulation infusion and vacuum holes are located on the non-expandable shaft section between the expandable balloon sections.

To demonstrate the effectiveness of the new assembly method when extra space is minimized, similar balloon diameter combinations were employed (FIG. 8A vs. FIG. 7). L(ii) represented in FIG. 8A is L(i) or L(ii). In an expanded state, the cones of the adjacent balloons are now contacting each other more intimately, thus minimizing the extra space. Again, the formulation is delivered between the balloons and will fill the space above the small diameter balloon section/area.

This new balloon assembly method can be described by the difference in balloon length before and after top assembly. Here, balloon length L(i) is defined as the length from the transition point of the distal waist/cone to that of the proximal cone/waist prior to shaft assembly; and balloon length L(ii) is defined as the length from the transition point of the distal waist/cone to that of the proximal cone/waist following shaft assembly. In this new assembly method, balloon waists were placed inside cones, or in some cases inside the balloon body as well if the cone length was short. The relationships between L(i) and L(ii) are:
 (1). L(i)=L(ii); if the balloon is assembled using a conventional method.
 (2). L(i)>L(ii); if the balloon is assembled using the new method.

Depending upon the length of the balloon cone, this new infusion catheter would have the cone/waist transition point at least at 25% inside the cone, or at 50 or 100% inside the cone, or partially or completely inside the balloon body.

For illustration purposes, consider an example involving an 8×20 mm balloon with a 5 mm cone length on both the distal and proximal sides. In this case, L(i)=body length+distal cone length+proximal cone length=20+5+5=30 mm. Situation 1: if the cone/waist transition points are placed 50% inside the cone, then L(ii)=20+2.5+2.5=25 mm; L(i) >L(ii). Situation 2: if the cone/waist transition points are placed 100% inside the cone or at the transition line of the cone/body, then L(ii)=20+0+0=20 mm; L(i)>L(ii), If the waist is further placed inside, then it would be situated inside the balloon body.

In the multiple balloon assembly on the catheter, the balloons having the same L(i) could also have the same L(ii) or a different one.

In another embodiment, a regular cone-shaped balloon can be used for this catheter. A round or radius cone balloon may also be used, however, because of its short cone length and potential for more contact surface area between adjacent cones.

Figure 8B:
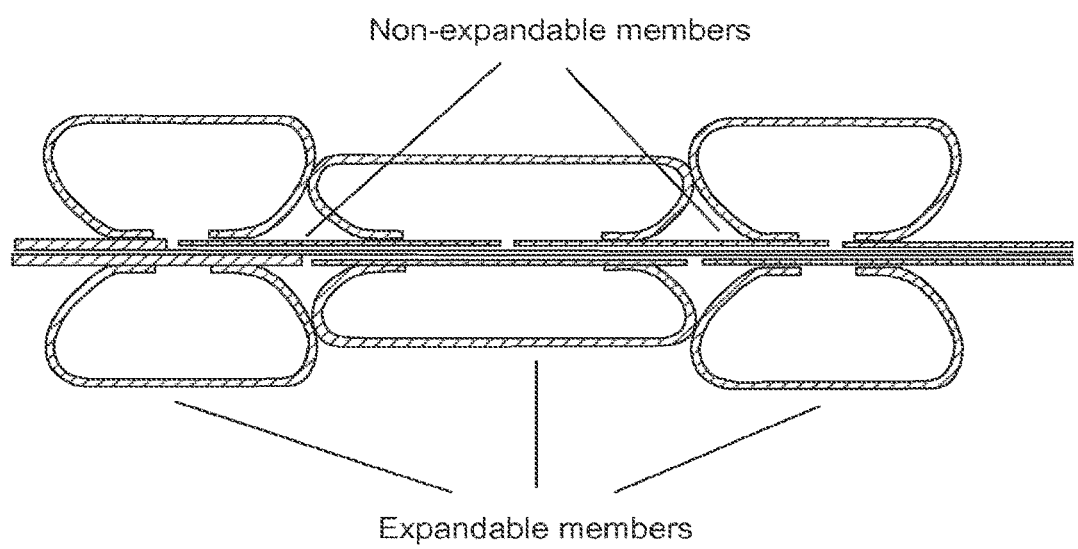
FIG. 8B is an embodiment of a partial cross-sectional view of a tri-balloon infusion device with differing balloon waist orientations for balloon attachment on a shaft.

In one embodiment, as shown in FIG. 8B, balloons can be attached onto the shaft by placing the balloon waists inside or partially inside the balloon body with inverted balloon waists. The inverted balloon waists would make the balloon cone more naturally rounded and would allow for more contact surface area between the cones; in addition, the waists could more easily be placed inside the balloon body.

Figure 9A:
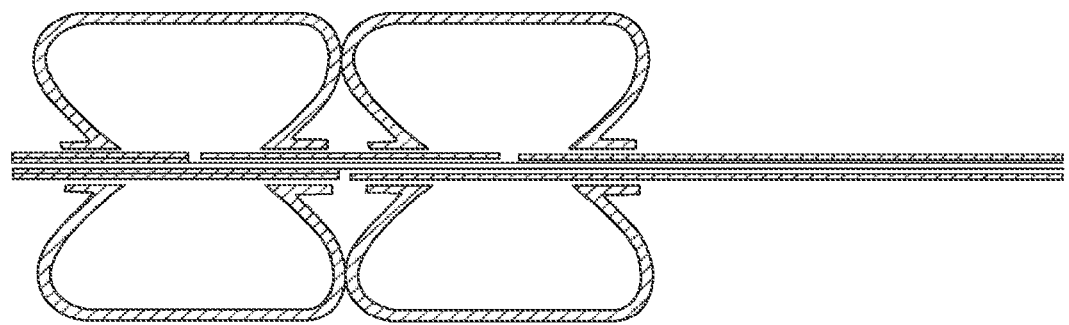
FIG. 9A is an embodiment of a partial cross-sectional view of an expanded double-balloon infusion device with infusion port(s) between the balloons.

In one embodiment, when a narrow treatment band or shorter overall balloon length is required, a double-balloon combination is used. FIG. 9A displays the two balloons having contacted adjacent cones in an expanded state. A chemical agent could be delivered through the delivery port on the shaft located between the two balloons. The formulation infusion and/or vacuum holes are located on the non-expandable shaft section between the expandable balloon sections. The chemical agent could remain in the middle narrow section of the two balloons during treatment. Optionally, the additional port could be available for flushing or vacuuming purposes. The two balloons on the catheter could also have their own inflation lumen, and, thus, could be inflated independently.

Figure 9B:
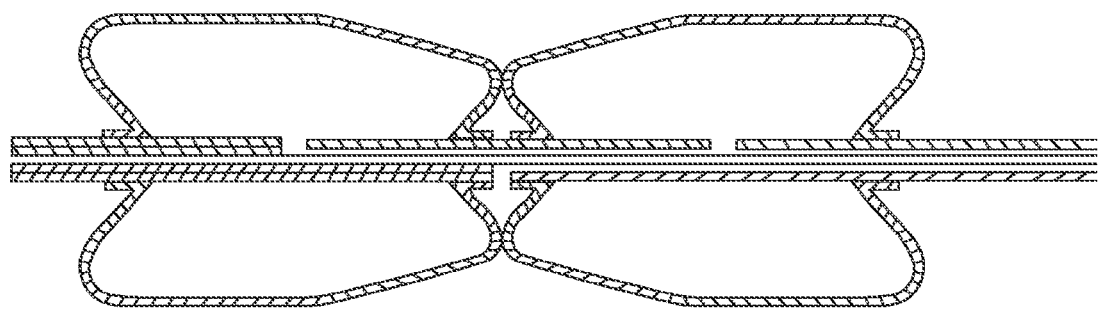
FIG. 9B is an embodiment of a partial cross-sectional view of an expanded double-balloon infusion device with a tapered diameter change and a smaller diameter in the middle section of the double-balloon.
Figure 9C:
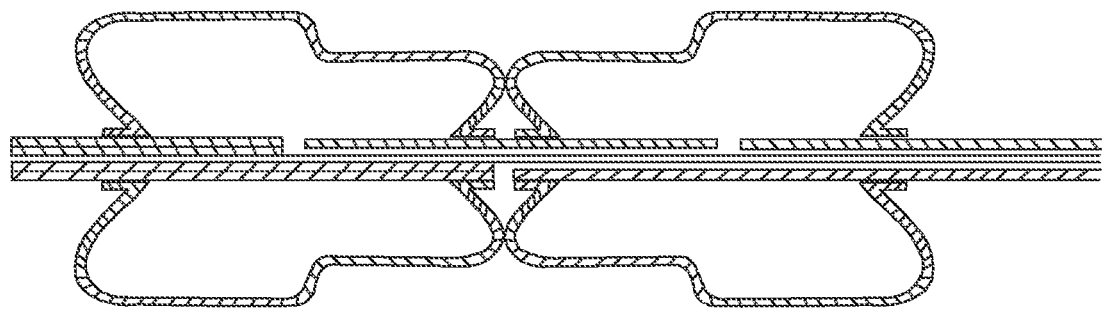
FIG. 9C is an embodiment of a partial cross-sectional view of an expandable double-balloon infusion device with combined two-stage balloons and a smaller diameter in the middle section of the double-balloon assembly.

In another embodiment, shown in FIGS. 9B-9C, a dual-diameter balloon can be used for the infusion catheter to achieve a wider treatment length despite a shorter overall balloon length. This balloon has two diameters that are smaller on one side relative to the other. Employing the same assembly technique as in the three-balloon arrangement, the dual-diameter balloons are attached on the shaft with the smaller diameter sides assembled head-to-head to form a smaller diameter middle section. The two ends of the large diameter sections confine the chemical agent primarily to the middle smaller diameter section to achieve a controlled volume delivery. The formulation infusion and/or vacuum holes are located on the non-expandable shaft section between the expandable balloon sections. Again, the formulation is delivered through the infusion holes on the non-expandable shaft section between the two expandable balloon sections.

One of the dual-diameter balloons is the tapered balloon shown in FIG. 9B. This two-balloon configuration has smaller diameter ends located in the middle of the two balloons facing head-to-head to each other. The resulting overall diameter of the middle section is smaller than that of the ends.

Another dual-diameter balloon is assembled from two-stage balloons, as shown in FIG. 9C. There are two distinct diameters in one balloon, i.e., one side of the balloon is bigger than the other; and there is an abrupt diameter change between the two diameters. Two-stage balloons can be assembled with the smaller diameter sides facing each other (FIG. 9C) and forming the middle of the overall balloon. The stage balloon can provide a wider treatment length despite having the same overall balloon length as in FIG. 9B.

Figure 10A:
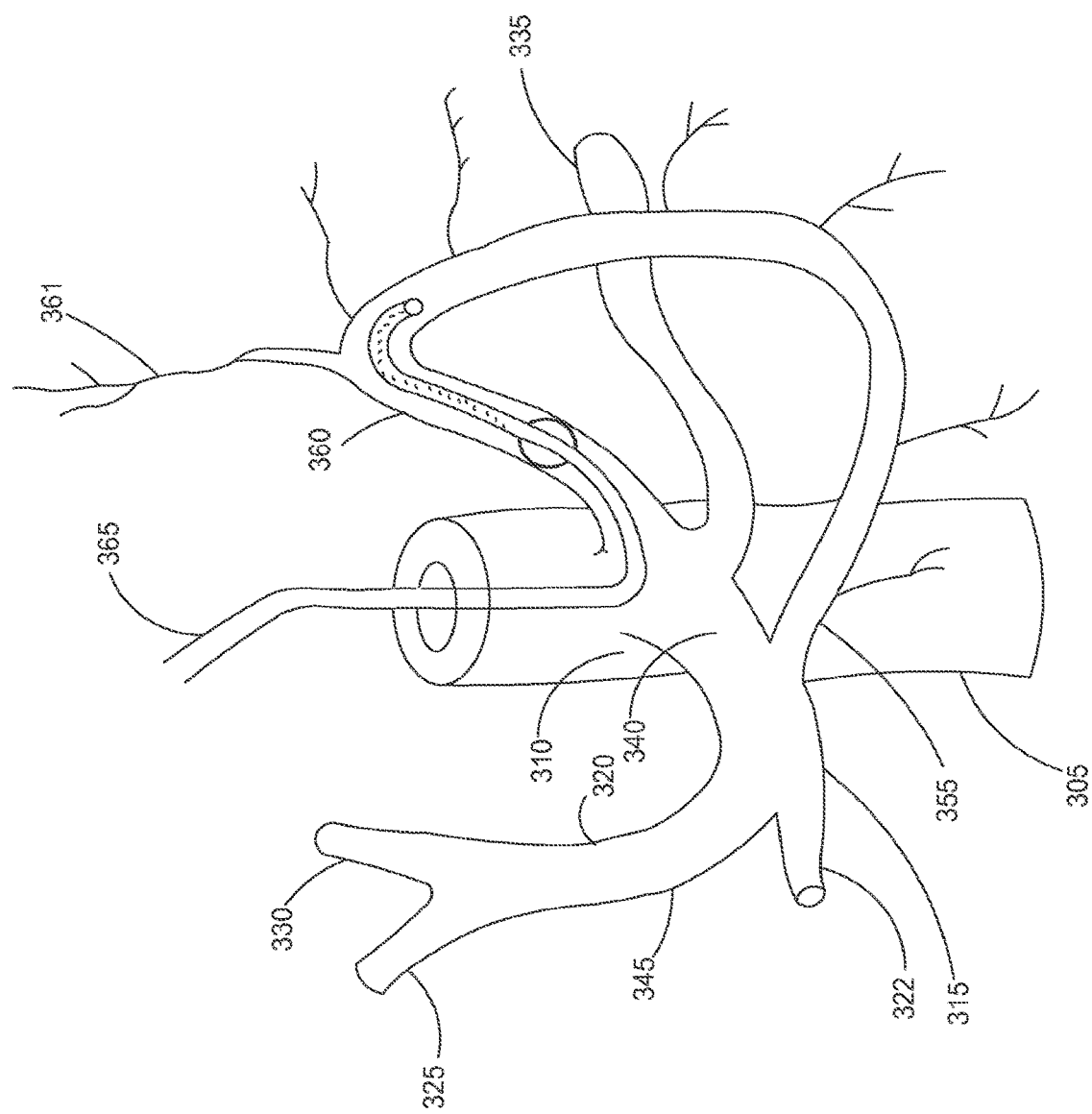
FIG. 10A is an embodiment of a formulation infusion to the left gastric arteries with a single balloon delivery catheter.
Figure 10B:
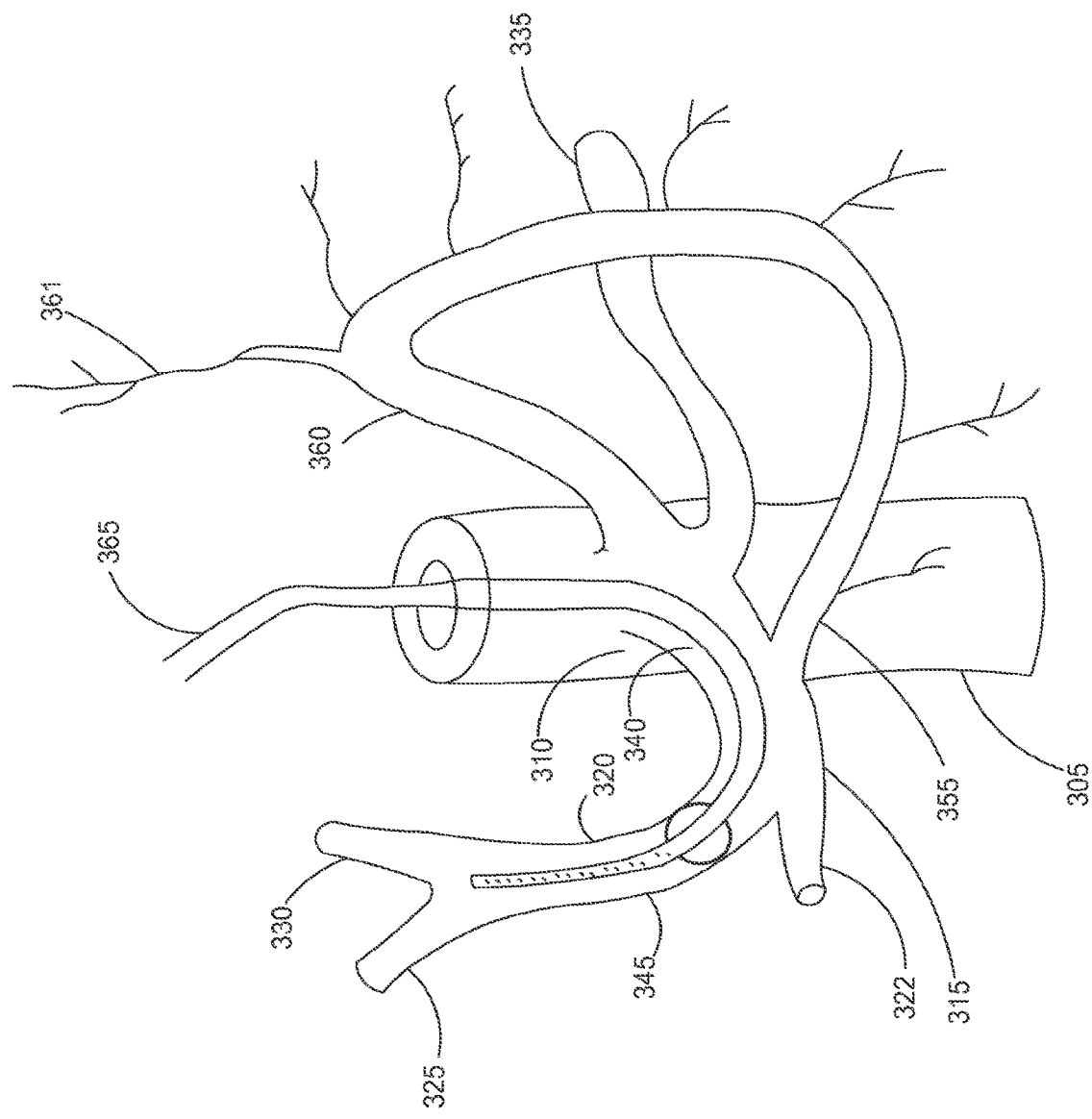
FIG. 10B is an embodiment of a formulation infusion to the hepatic arteries with a single balloon delivery catheter.
Figure 11:
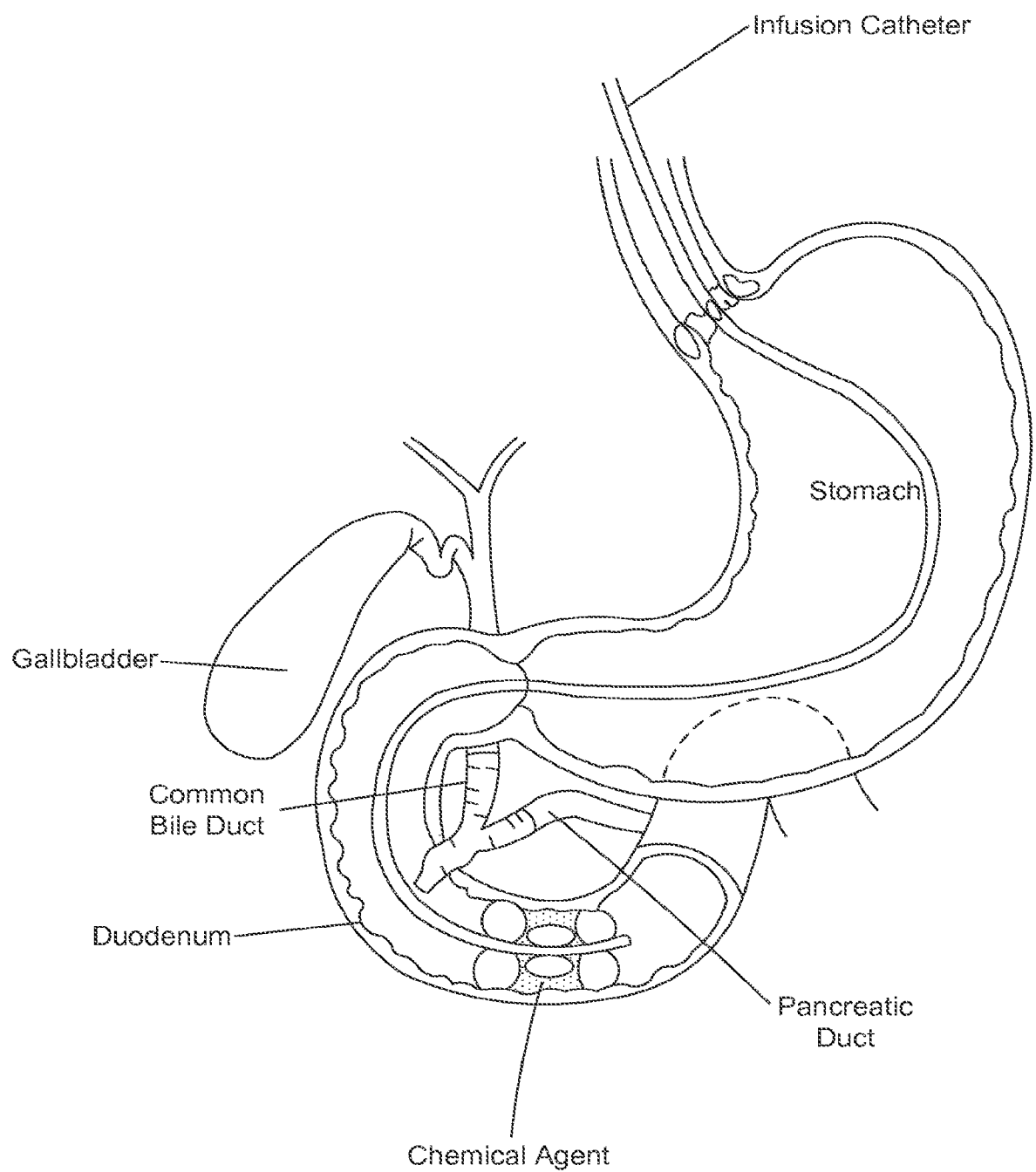
FIG. 11 is an embodiment of a formulation infusion to the duodenum with a triple-balloon delivery catheter.

FIGS. 10A and 10B illustrate balloon infusion catheter 365 is positioned in a gastric artery 360 or a hepatic artery 320. Various arteries surrounding the liver and stomach as well as the various nerve systems that innervate the liver and stomach and their surrounding organs and tissues are shown in FIGS. 10A and 10B. The arteries surrounding the liver and stomach include the abdominal aorta 305, the celiac artery 310, the common 315 and proper hepatic arteries 320, the gastroduodenal artery 322, the right 325 and left hepatic arteries 330, the splenic artery 335 and esophageal branches 361. The various nerves that innervate the liver and stomach and their surrounding organs and tissues include the celiac 340 and hepatic plexuses 345. Blood supply to the liver is pumped from the heart into the aorta and then down through the abdominal aorta 305 and into the celiac artery 310. From the celiac artery 310, blood travels through the common hepatic artery 315, into the proper hepatic artery 320, then into the liver through the right 325 and left hepatic arteries 330. The common hepatic artery 315 branches off from the celiac trunk and gives rise to gastroduodenal arteries. The nerves innervating the liver include the celiac plexus 340 and the hepatic plexus 345. The celiac plexus 340 wraps around the celiac artery 310 and continues into the hepatic plexus 345, which wraps around the proper 320 and common hepatic arteries 315, and/or continues on to the right 325 and left hepatic arteries 330. In some anatomies, the celiac 340 and hepatic plexuses 345 adhere tightly to the walls of the arteries, supplying the liver with blood, thereby rendering intra-to-extra-vascular neuromodulation particularly advantageous. In several embodiments, the media thickness of vessels (e.g., the hepatic artery) ranges from about 0.1 cm to about 0.25 cm. In some embodiments, the formulations may be delivered to the inner wall of the target vessel or target nerves. Intravascular delivery may be employed, because the nerves tightly adhere to the outer walls of the arteries, thus supplying blood to the liver (e.g. in the case of the hepatic artery branches).

The arteries surrounding the stomach include the abdominal aorta 305, the celiac artery 310, the right 355 and left gastric arteries 360, and the esophageal branches 361. Blood supply to the stomach is pumped from the heart into the aorta and then down through the abdominal aorta 305 and into the celiac artery 310. From the celiac artery 310, blood travels through the right gastric artery 355 and left gastric artery 360, the esophageal branches 361, and into the stomach.

With continued reference to FIGS. 10A and 10B, the hepatic plexus 345 is the largest offset from the celiac plexus 340. The hepatic plexus 345 is believed to primarily carry afferent and efferent sympathetic nerve fibers, the stimulation of which can increase blood glucose levels by a number of mechanisms. For example, stimulation of sympathetic nerve fibers in the hepatic plexus 345 can increase blood glucose levels by enhancing hepatic glucose production, or by reducing hepatic glucose uptake. Disruption of sympathetic nerve signaling in the hepatic plexus 345 can, therefore, alter levels of blood glucose.

In one embodiment, FIG. 10B depicts a schematic view of a balloon delivery catheter positioned within the hepatic artery for treatment of diabetes. In another embodiment, FIG. 10A depicts a schematic view of a balloon delivery catheter positioned within the left gastric artery for treatment of obesity and diabetes.

Certain embodiments of the invention include delivering a vapor or liquid formulation to the segment of the body lumen at a specific delivery rate for a pre-determined duration. The formulation may be heated to at least 80° C., for example, 100° C. or 150° C., prior to delivery. The catheter materials, specifically the balloon and shafts, should be functional at the above temperatures, as such materials are made to withstand high temperatures. In certain embodiments, delivered vapors can undergo a phase change to liquid, resulting in a release of energy, which is transferred to the tissue.

In certain embodiments, for example, the safe and effective dose for treating the tissue ranges from about 2 cal/g to about 150 cal/g., or from about 5 cai/g to about 100 cal/g, and the energy flow rate of the delivery system ranges from about 2 cal/g to about 500 cal/sec, or from about 5 cal/sec to about 150 cal/sec. In one embodiment, the formulation generator creates a vapor or liquid formulation, with a pressure that ranges from about 2 psi to 200 psi and a temperature that ranges from about 20° C. to 150° C., or from about 50° C. to 120° C.

A safe and effective amount of formulation and/or energy should be applied in order to satisfactorily injure tissues. In general, the dose amount correlates with the degree of injury to the tissue.

In some embodiments, an effective dose of energy ranges from about 1 to about 100 cal/g and/or an effective formulation dose ranges from 0.2 microliters to 200 milliliters. These dosing limitations may vary as other delivery parameters (e.g., delivery rate or duration, etc.) may call for different doses to accomplish the ultimate injury benefit.

Following dose determination, the total amount of energy (cals) or formulation (mls) applied via a delivery system should be determined. This value is calculated by multiplying dose (cal/g) by the amount of tissue to be treated (grams).

The delivery/flow rate, or the rate at which the delivery system delivers the formulation, generally determines the duration of formulation. For example, at a delivery rate of 30 cals/sec, a treatment duration of 10 seconds would be necessary to deliver 300 calories. The delivery rate generally ranges from about 2 to about 200 cals/sec. Again, these limitations are not definite and can change depending on treatment and/or delivery parameters.

Treatment times can vary depending on the volume of the tissue to be treated, and the intended degree of injury to the target tissue. Treatment times can vary from about 2 seconds to about 60 minutes. In some embodiments for inducing injury to relieve symptoms, the safe and effective treatment time ranges from about 4 seconds to about 30 minutes.

The delivery rate can be set by regulating the delivery system. Once the user establishes the delivery rate, formulation resources will determine the amount of pressure necessary to deliver the vapor or liquid at the desired rate. Changing the delivery rate setting will cause the formulation generator to adjust the amount of pressure delivered. The pressure in the vapor generator can range from about 5 psi to about 200 psi, or from about 10 psi to about 50 psi.

In one embodiment, the method for treatment of hypertension includes inserting a delivery catheter percutaneously into the renal artery adjacent to the nerves; using the catheter to infuse the formulation described above and/or heat to the tissue of the body lumen adjacent to the nerves, wherein the amount of the formulation and/or heat delivered is effective to injure or damage the nerves, such as, for instance, by lowering blood pressure; and, lastly, withdrawing the delivery catheter from the body lumen. The purpose of the heat is to enhance the injury/damage effect by accelerating the reaction rate between the formulation and nerves. Potential formulations include gases, vapors, liquids, solutions, emulsions, and suspensions of one or more ingredients. If the formulation includes vapors of one or more ingredients, the heat may be generated by condensation of the vapors into liquids in the tissue. If the formulation includes liquids or solutions, the heat may be transferred from the high temperature formulations that exceed body temperature. The formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure may range from 0.1 atm to 14 atm, from 3 atm to 10 atm, or from 4 atm to 8 atm.

In one embodiment, the method for treatment of asthma includes inserting a delivery catheter into the airways adjacent to the nerves; using the catheter to infuse the formulation described above and/or heat to the tissue of the airway adjacent to the nerves, wherein the amount of the formulation and/or heat delivered is effective to injure or damage the nerves, such as, for instance, by relieving shortness of breath; and, lastly, withdrawing the delivery catheter from the body lumen. The purpose of the heat is to enhance the injury/damage effect by accelerating the reaction rate between the formulation and nerves. Potential formulations include gases, vapors, liquids, solutions, emulsions, and suspensions of one or more ingredients. If the formulation includes vapors of one or more ingredients, the heat may be generated by condensation of the vapors into liquids in the tissue. If the formulation includes liquids or solutions, the heat may be transferred from the high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure may range from 0.1 atm to 14 atm, from 3 atm to 10 atm, or from 4 atm to 8 atm.

In one embodiment, the method for treatment of a COPD includes inserting a delivery catheter into the airway adjacent to the nerves; using the catheter to infuse the formulation described above and/or heat to the tissue of the body lumen adjacent to the nerves, wherein the amount of the formulation and/or heat delivered is effective to injure or damage the nerves, such as, for instance, by relieving COPD symptoms; and, lastly, withdrawing the delivery catheter from the airway. The purpose of the heat is to enhance the injury/damage effect by accelerating the reaction rate between the formulation and nerves. Potential formulations include gases, vapors, liquids, solutions, emulsions, and suspensions of one or more formulations. If the formulation includes vapors of one or more ingredients, the heat may be generated by condensation of the vapors into liquids. If the formulation includes liquids or solutions, the heat may be transferred from the high temperature formulations that exceed body temperature. The formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure and/or the balloon inflation pressure may range from 0.1 atm to 14 atm, from 3 atm to 10 atm, or from 4 atm to 8 atm.

In one embodiment, the method for treatment of diabetes includes inserting a delivery catheter percutaneously into the hepatic arteries adjacent to the nerves, specifically the hepatic celiac artery, proper hepatic arteries, and the left and right hepatic arteries; using the catheter to infuse the formulation described above and/or heat to the tissue of the body lumen adjacent to the nerves, wherein the amount of the formulation and/or heat delivered is effective to injure or damage the nerves, such as, for instance, by lowering glucose level; and, lastly, withdrawing the delivery catheter from the body lumen. The purpose of the heat is to enhance the injury/damage effect by accelerating the reaction rate between the formulation and nerves. Potential formulations include gases, vapors, liquids, solutions, emulsions, and suspensions of one or more ingredients. If the formulation includes vapors of one or more ingredients, the heat may be generated by condensation of the vapors into liquids in the tissue. If the formulation includes liquids or solutions, the heat may be transferred from the high temperature formulations that exceed body temperature. The formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure and/or the balloon inflation pressure may range from 0.1 atm to 14 atm, from 3 atm to 10 atm, or from 4 atm to 8 atm.

In one embodiment, the method for treatment of obesity and diabetes includes inserting a delivery catheter into the left and/or right gastric arteries adjacent to the stomach and esophageal nerves; using the catheter to infuse the formulation described above and/or heat to the tissue of the gastric arteries adjacent to the nerves, wherein the amount of the formulation and/or heat delivered is effective to injure or damage the nerves such as, for instance, by lowering body weight; and, lastly, withdrawing the delivery catheter from the gastric arteries. Potential formulations include gases, vapors, liquids, solutions, emulsions, and suspensions of one or more ingredients. If the formulation includes vapors of one or more ingredients, the heat may be generated by condensation of the vapors into liquids. If the formulation includes liquids or solutions, the heat may be transferred from the high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure and/or the balloon inflation pressure may range from 0.1 atm to 14 atm, from 3 atm to 10 atm, or from 4 atm to 8 atm.

In one embodiment, the method for treatment of obesity and diabetes includes inserting a delivery catheter percutaneously into the hepatic arteries adjacent to the nerves, specifically the hepatic celiac artery, the proper hepatic arteries, and the left and right hepatic arteries; using the catheter to infuse the formulation described above and/or heat to the tissue of the hepatic arteries adjacent to the nerves; withdrawing the delivery catheter from the hepatic arteries; inserting a delivery catheter into the left and/or right gastric arteries adjacent to the stomach and esophageal nerves; using the catheter to infuse the formulation described above and/or heat to the tissue of the gastric arteries adjacent to the nerves, wherein the amount of the formulation and/or heat delivered is effective to injure or damage the nerves, such as, for instance, by lowering body weight and glucose level; and, lastly, withdrawing the delivery catheter from the gastric arteries. Potential formulations include gases, vapors, liquids, solutions, emulsions, and suspensions of one or more ingredients. If the formulation includes vapors of one or more ingredients, the heat may be generated by condensation of the vapors into liquids. If the formulation includes liquids or solutions, the heat may be transferred from the high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure and/or the balloon inflation pressure may range from 0.1 atm to 14 atm, from 3 atm to 10 atm, or from 4 atm to 8 atm.

In one embodiment, the method for treatment of obesity includes inserting a delivery catheter into the digestive lumen adjacent to the nerves; using the catheter to infuse the formulation described above and/or heat to the tissue of the digestive lumen, wherein the amount of the formulation and/or heat delivered is effective to injure or damage the tissue, such as, for instance, by lowering body weight; and, lastly, withdrawing the delivery catheter from the digestive lumen. Potential digestive lumens for this embodiment include the esophagus, the stomach, the duodenum, the jejunum, the small and large intestines, and the colon. The purpose of the heat is to enhance the injury/damage effect by accelerating the reaction rate between the formulations and nerves. Potential formulations include gases, vapors, liquids, solutions, emulsions, and suspensions of one or more ingredients. If the formulation includes vapors of one or more ingredients, the heat may be generated by condensation of the vapors into liquids. If the formulation includes liquids or solutions, the heat may be transferred from the high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C.

In one embodiment, the method for treatment of obesity and diabetes includes inserting a delivery catheter into the left and/or right gastric arteries adjacent to the stomach and esophageal nerves; using the catheter to infuse the formulation described above and/or heat to the tissue of the gastric arteries adjacent to the nerves, wherein the amount of the formulation and/or heat delivered is effective to injure or damage the nerves, such as, for instance, by lowering body weight; and, lastly, withdrawing the delivery catheter from the gastric arteries. Potential formulations include gases, vapors, liquids, solutions, emulsions, and suspensions of one or more ingredients. If the formulation includes vapors of one or more ingredients, the heat may be generated by condensation of the vapors into liquids. If the formulation includes liquids or solutions, the heat may be transferred from the high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C.

In one embodiment, the method for treatment of obesity and/or diabetes includes inserting a delivery catheter orally via the mouth, esophagus and stomach into the duodenum and/or jejunum; using the catheter to infuse the formulation described above and/or heat to the surface tissue of the duodenum and/or jejunum for 1-30 minutes, wherein the amount of the formulation and/or heat delivered is effective to injure or damage the surface, the tissue and the nerves of the body lumen, such as the duodenum or jejunum, for instance, by lowering body weight and glucose level; optionally removing or withdrawing the formulation; and, lastly, withdrawing the delivery catheter from the digestive lumen, such as the duodenum or jejunum. Potential formulations include gases, vapors, liquids, solutions, emulsions, and suspensions of one or more ingredients. If the formulation includes vapors of one or more ingredients, the heat can be generated by condensation of the vapors into liquids. If the formulation includes liquids or solutions, the heat can be transferred from the high temperature formulations that exceed body temperature. The formulation infusion pressure and/or the balloon inflation pressure may range from 0.1 atm to 14 atm, from 3 atm to 10 atm, or from 4 atm to 8 atm. The liquid formulation temperature may range from −40° C. to 140° C., from −30° C. to 100° C., or from −20° C. to 80° C. The temperature of the treated tissue, which, in this case is the surface tissue, may be lower than the temperature of the formulation and higher than body temperature. The temperature of the treated tissue may range from −40° C. to 100° C., from −30° C. to 90° C., from 36° C. to 80° C., or from 60° C. to 80° C. Treatment entails modifying the surface of the duodenum or jejunum. Therapeutic benefits such as lowering of body weight, glucose levels, and/or HbA1c (A1C) levels, depend on formulation dose and temperature, length of treatment period, and the surface area and thickness of the treated duodenum. For safety reasons, perforation of the duodenum is not encouraged. Treating the surface modifies the morphology, the nerves, and food absorption capacity of the duodenum.

In one embodiment, the method for treatment of obesity and/or diabetes includes non-invasively inserting an infusion catheter orally via the mouth, esophagus and stomach into the duodenum and/or jejunum; using the catheter to infuse chemical agents to the surface tissue of the duodenum and/or jejunum for 1-10 minutes, wherein the amount of the chemical agent delivered is effective to injure or damage the surface, the tissue and the nerves of the body lumen, such as the duodenum or jejunum, for instance, by lowering body weight and glucose level; optionally removing or withdrawing the agents; and, lastly, withdrawing the delivery catheter from the digestive lumen, such as the duodenum or jejunum. The chemical agent includes the formulation of chemical agents and/or absolute ethanol. Below are descriptions of pre-clinical trials for the treatment of obesity and/or diabetes.

All infusion catheters in the embodiments described above are applicable to the following studies. For instance, in one study, the 2-3-groove dumbbell-type balloons with 4-holes per groove were used for the treatment of obesity and/or diabetes. Balloon diameters and lengths ranged from 12 to 15 mm and from 55 to 80 mm, respectively. The study was conducted according to the procedure described above. Two juvenile Yorkshire cross pigs (each weighing about 9 kg) were anesthetized with isoflurane. An infusion balloon catheter was inserted via the mouth, stomach and pylorus into the duodenum under guidance of a pediatric endoscope and fluoroscope. The ligament of treitz was used as the anatomical mark for the distal end of the duodenum. Upon delivery of the infusion balloon catheter to the duodenum, 1.5 to 2.0 ml of absolute ethanol was injected after rapid pre-inflation of the balloon up to 1.5 atm. Balloon pressure was then held at 0.5 atm or less for 1 to 2 min. The treatment agent played dual roles in this procedure: (1) inflation of the balloon and (2) delivery of the chemical to the target vessel tissue through the holes on the balloon wall. After treatment, the balloon was partially deflated and pulled back to a defined distance to avoid overlapping with the next treatment location. Treatment was then repeated. The bile duct was not treated. The animal was euthanized 2 hours after treatment. The duodenal tissue was examined and suspended in triphenyl tetrazolium chloride (TTC) solution for 30 minutes. Following chemical treatment, the necrotized tissue may display white-colored spots.

The chemical agents used in the above described study were pure acetic acid and absolute ethanol. Treatment efficacy was clearly demonstrated in the TTC-stained duodenal tissues from both treated animals, as white-colored spots were localized to chemically-ablated regions.

Following the success of the above acute study, a chronic study was conducted to demonstrate the clinical benefits of the treatment. The study included seven pigs of similar weight as in the acute study above. Three of the seven pigs were treated with absolute ethanol, three with acetic acid, and one sham pig with saline. The same procedure as described in the previous acute study was employed for treatment with absolute ethanol. As before, after the infusion balloon catheter reached the duodenum, the balloon was rapidly pre-inflated with absolute ethanol up to a pressure of 1.5 atm; about an additional 1.5 ml to 2.0 ml of ethanol was next injected through the balloon wall into the duodenum, and pressure was then held for 2 min at 0.5 atm or below. Once the treatment period ended, the treated duodenal section was then flushed with about 10 ml of water using the endoscope.

Figure 13:
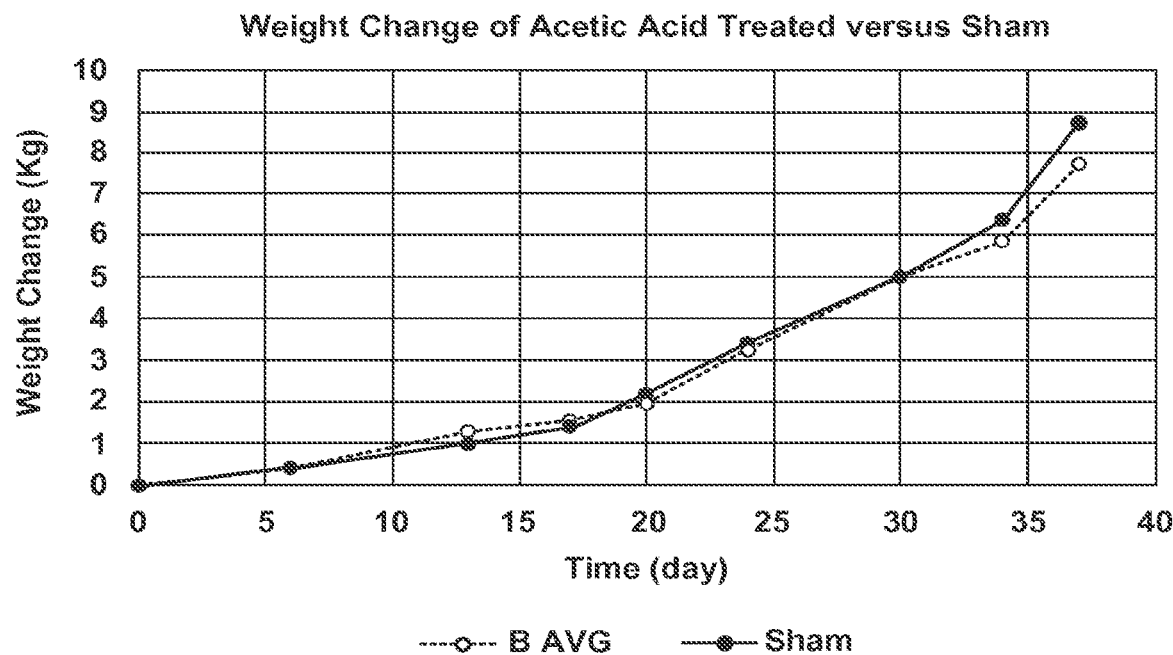
FIG. 13 is a curve demonstrating weight change following duodenal treatment with an acetic acid agent.

Treatment with acetic acid proceeded similarly to that with absolute ethanol. As before, the pig duodena were treated, this time at a dose of 0.5 ml for 1 minute. After each treatment, balloons were partially deflated and pulled back to a pre-defined distance to avoid overlapping treatment with the next treatment location. Treatment was then repeated. The bile duct was not treated. Animals were recovered for chronic observation and evaluation, Pigs that underwent duodenal treatment with acetic acid were euthanized about five weeks after treatment. The animals were determined to be healthy following clinical and pathological evaluation. As demonstrated in FIG. 13, treatment of the duodenum with acetic acid did not have significant weight difference in comparison with that of the sham animals. Glucose levels fluctuated and were inconclusive.

Figure 14:
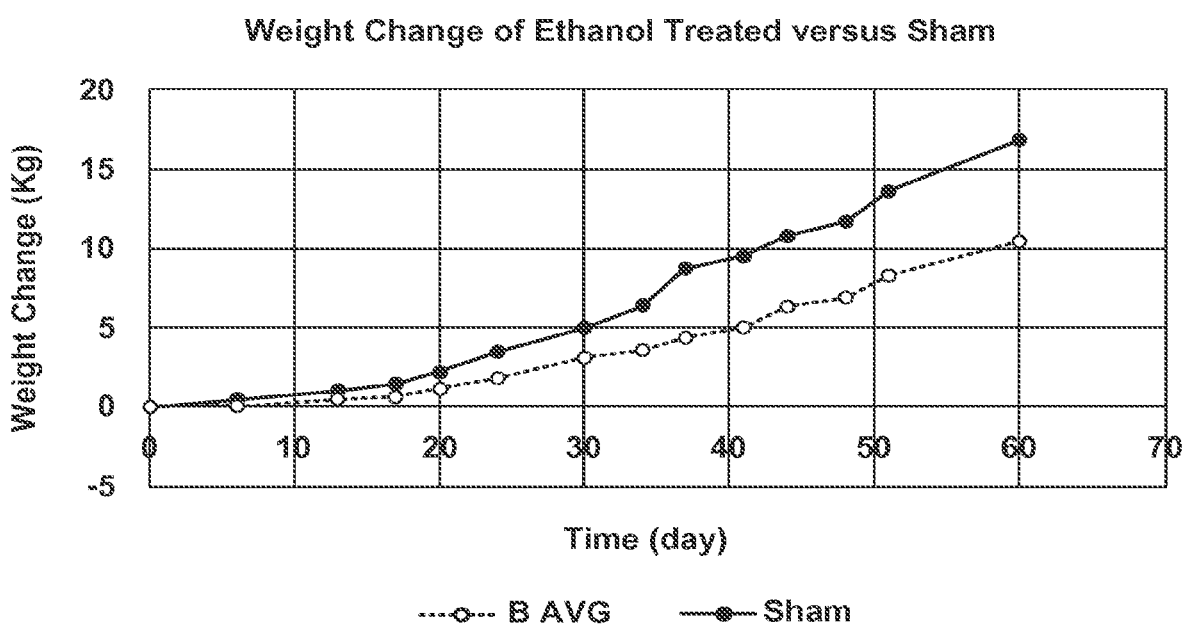
FIG. 14 is a curve demonstrating weight change following duodenal treatment with an ethanol agent.

Pigs that underwent duodenal treatment with absolute ethanol were euthanized about eight weeks after treatment. The animals were determined to be healthy following clinical and pathology evaluation. As demonstrated in FIG. 14, treatment of the duodenum with absolute ethanol resulted in less animal weigh increases in comparing with the sham animal. Glucose levels were inconclusive.

In one embodiment, the method for treatment of Barrett's esophagus disease includes an infusion balloon device, a procedure, and a chemical agent. In this method, a balloon infusion catheter is inserted non-invasively via the mouth into the esophagus under pediatric endoscopic guidance. 15 mm balloons are typically used at a length ranging from 55 to 80 mm, with 3 grooves in the middle section and 4 micro-holes per groove for chemical infusion. Once balloons localize to the target esophagus, they are rapidly pre-inflated to full size at a pressure up to 1.5 atm. Examples of doses delivered are as follows: (1) for treatment with absolute ethanol, 1.5 ml are delivered at the distal portion of the esophagus for 4 min and at the proximal portion for 2 min; (2) for treatment with acetic acid, 0.5 ml are delivered at the distal portion of the esophagus for 2 min and at the proximal portion for 1 min. Once the treatment period ends, treated sites are flushed with about 10 ml of water using an endoscope channel. Following each treatment, balloons are partially deflated and moved to other locations for additional treatments.

Using the above described procedure, a chronic study was conducted with seven juvenile Yorkshire cross pigs. Three of the seven pigs were treated with absolute ethanol, three with acetic acid, and a sham with saline. Endoscopic examinations were performed before and after treatment. Animals were recovered for chronic observation and evaluation. Animals were also endoscopically examined after two weeks of treatment and were reexamined and euthanized after four weeks. Effects of treatment were assessed by the endoscopic exam. In acetic acid-treated esophageal sections, severe stricture phenomena were observed. Histopathological analysis of treated sections demonstrated epithelial thickening and complete epithelization except for in the acetic acid-treated group, where the epithelial layer was, at times, absent.

The above pre-clinical findings demonstrate that ethanol treatment is effective and safe. Acetic acid treatment, on the other hand, led to severe narrowing and stricture in the treated esophagus. In addition, no difference in weight change was observed in duodenal-treated animals compared with untreated animals. It is well known that acid erodes and damages esophageal linings; acetic acid produced lesions in the duodenal wall following topical application. These observations indicate that acetic acid may not be suitable for duodenal and esophageal treatment.

In one embodiment, the method for treatment of urological diseases and/or benign prostate hyperplasia (BPH) includes inserting a delivery catheter into the urological lumen; using the catheter to infuse the formulation described above and/or heat to the lumen of a urological tissue, e.g. the prostate, urethra, and ureter, wherein the amount of the formulation and/or heat delivered is effective to injure or damage the tissue, such as, for instance, by controlling the flow of urine; and, lastly, withdrawing the delivery catheter from the urological lumen. The purpose of the heat is to enhance the injury/damage effect by accelerating the reaction rate between the formulation and nerves. The formulations include one of gases, vapors, liquids, solutions, emulsions, and suspensions of one or more ingredients. If the formulation includes vapors of one or more ingredients, the heat can be generated by condensation of the vapors into liquids. If the formulation includes liquids or solutions, the heat can be transferred from high temperature formulations that exceed body temperature. The liquid formulation temperature may range from −40° C. to 140° C., from −30° C. to 100° C., or from −20° C. to 80° C. The temperature of the treated tissue adjacent to the nerves may be lower than the formulation temperature and higher than body temperature. The temperature of the treated tissue adjacent to the nerves may range from −40° C. to 100° C., from −30° C. to 90° C., or from −20° C. to 80° C. The formulation infusion pressure and/or the balloon inflation pressure may range from 0.1 atm to 14 atm, from 3 atm to 10 atm, or from 4 atm to 8 atm.

In one embodiment, the method for treatment of cancers or tumors includes inserting a needle or needle-based catheter percutaneously or transorally into the cancers or tumors under imaged guide; using the catheter to infuse the formulation described above and/or heat to the cancer tissues of the human body, wherein the amount of the formulation and/or heat delivered is effective to injure, damage or eliminate the cancer tissues, such as, for instance, by shrinking or eliminating the tumors; and, lastly, withdrawing the delivery catheter from the body. Potential imaging guides include ultrasound, X-ray, CT scan, NMR imaging, and scopes. Relevant cancers include adrenal, bladder, cervical, colon, esophageal, gallbladder, kidney, liver, lung, ovarian, pancreatic, prostatic, rectal, stomach, and uterine. The purpose of the heat is to enhance the injury/damage/elimination effect by accelerating the reaction rate between the formulation and cancer tissues. The formulations include one of gases, vapors, liquids, solutions, emulsions, and suspensions of one or more ingredients. If the formulation includes vapors of one or more ingredients, the heat may be generated by condensation of the vapors into liquids in the tissue. If the formulation includes liquids or solutions, the heat may be transferred from the high temperature formulations that exceed body temperature. The formulation temperature may range from −40° C. to 140° C., from −30° C. to 100° C., or from −20° C. to 80° C. The temperature of the treated tissue may be lower than the formulation temperature and higher than body temperature. The temperature of the treated tissue may range from −40° C. to 100° C., from −30° C. to 90° C., or from −20° C. to 80° C.

What is claimed is:

1. A method for treating diabetes and obesity, the method comprising:
    inserting a first delivery catheter that is a needle catheter or a needle-based catheter into a first treatment site in a common hepatic artery;
    infusing a chemical formulation from a formulation infusion lumen of the first delivery catheter to a tissue of the body lumen at the first treatment site, wherein the chemical formulation infused is effective to injure and/or damage the tissue at the first treatment site;
    withdrawing the first delivery catheter from the first treatment site;
    inserting a second delivery catheter that is the same or different as the first delivery catheter and that is a needle catheter or a needle-based catheter into a second treatment site in the common hepatic artery, wherein the second treatment site is a different treatment site than the first treatment site;
    infusing a chemical formulation from a formulation infusion lumen of the second delivery catheter to a tissue of the body lumen at the second treatment site, wherein the chemical formulation infused is effective to injure and/or damage the tissue at the second treatment site; and
    withdrawing the second delivery catheter from the second treatment site;
    wherein the injury and/or damage to the tissue at the first treatment site and to the tissue at the second treatment site is effective to have a benefit of relieving symptoms comprising reduction of HbA1c (A1c), glucose level, and body weight; and
    wherein the first and/or second delivery catheter comprises a balloon around a circumference of a shaft and the formulation infusion lumen in the shaft that passes through a region of the shaft that comprises the balloon thereon.

2. The method of claim 1, wherein the method further comprises:
    inflating the balloon after the insertion to the first treatment site and deflating the balloon prior to the withdrawing from the first treatment site; and/or
    inflating the balloon after the insertion to the second treatment site and deflating the balloon prior to the withdrawing from the second treatment site.

3. The method of claim 1, wherein the chemical formulation comprises one or more ingredients chosen from water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, lipiodol, urea, and derivatives thereof.

4. The method of claim 1, wherein the chemical formulation comprises ethanol, acetic acid, ethanol and water, an ethanol/water azeotrope, or ethanol and acetic acid.

5. The method of claim 1, wherein the chemical formulation comprises ethanol.

6. The method of claim 1, wherein the method comprises infusing heat from the first and/or second delivery catheter to the tissue of the body lumen at the first and/or second treatment site.

7. The method of claim 1, further comprising:
inserting a third delivery catheter that is a needle catheter or a needle-based catheter into a third treatment site in a renal artery;
infusing a chemical formulation from a formulation infusion lumen of the third delivery catheter to a tissue of the body lumen at the third treatment site, wherein the chemical formulation infused is effective to injure and/or damage the tissue at the third treatment site; and
withdrawing the third delivery catheter from the third treatment site.

8. A method for treating diabetes and obesity, the method comprising:
inserting a first delivery catheter that is a needle catheter or a needle-based catheter into a first treatment site in a common hepatic artery;
infusing a chemical formulation from a formulation infusion lumen of the first delivery catheter to a tissue of the body lumen at the first treatment site, wherein the chemical formulation infused is effective to injure and/or damage the tissue at the first treatment site;
withdrawing the first delivery catheter from the first treatment site;
inserting a second delivery catheter that is the same or different as the first delivery catheter and that is a needle catheter or a needle-based catheter into a second treatment site in the common hepatic artery, wherein the second treatment site is a different treatment site than the first treatment site;
infusing a chemical formulation from a formulation infusion lumen of the second delivery catheter to a tissue of the body lumen at the second treatment site, wherein the chemical formulation infused is effective to injure and/or damage the tissue at the second treatment site;
withdrawing the second delivery catheter from the second treatment site;
inserting a third delivery catheter that is a needle catheter or a needle-based catheter into a third treatment site in a renal artery;
infusing a chemical formulation from a formulation infusion lumen of the third delivery catheter to a tissue of the body lumen at the third treatment site, wherein the chemical formulation infused is effective to injure and/or damage the tissue at the third treatment site; and
withdrawing the third delivery catheter from the third treatment site;
wherein the injury and/or damage to the tissue at the first treatment site, at the second treatment site, and at the third treatment site is effective to have a benefit of relieving symptoms comprising reduction of HbA1c (A1c), glucose level, and body weight.

* * * * *